United States Patent
Zechlin et al.

(10) Patent No.: US 12,023,448 B2
(45) Date of Patent: Jul. 2, 2024

(54) CONNECTION ARRANGEMENT FOR CONNECTING AN ANAESTHETIC CONTAINER TO AN ANAESTHETIC VAPORIZER

(71) Applicant: Drägerwerk AG & Co. KGaA, Lübeck (DE)

(72) Inventors: Jacob-Michael Zechlin, Lübeck (DE); Moritz Buchholz, Hamburg (DE); Daisy Cordelia Charlotte Prior, Cambridge (GB); Lucy Chandra Devi Fielding, Histon (GB); Thomas Kröplin, Süsel (DE); Frederick William Hamlin, Boston, MA (US); Alexander Roland Mauchle, Milton Keynes (GB)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 761 days.

(21) Appl. No.: 17/266,380

(22) PCT Filed: Jul. 19, 2019

(86) PCT No.: PCT/EP2019/069487
§ 371 (c)(1),
(2) Date: Feb. 5, 2021

(87) PCT Pub. No.: WO2020/030408
PCT Pub. Date: Feb. 13, 2020

(65) Prior Publication Data
US 2021/0290887 A1   Sep. 23, 2021

(30) Foreign Application Priority Data
Aug. 8, 2018 (DE) ..................... 10 2018 006 264.4

(51) Int. Cl.
*A61M 16/18* (2006.01)

(52) U.S. Cl.
CPC ................................ *A61M 16/186* (2013.01)

(58) Field of Classification Search
CPC .......... A61M 16/18–186; A61M 16/01; A61M 15/00; B65B 3/04; B65B 1/04
See application file for complete search history.

(56) References Cited

U.S. PATENT DOCUMENTS

| 5,287,898 A | 2/1994 | Falb et al. |
| 5,381,836 A * | 1/1995 | Braatz ................ A61M 16/183 141/366 |

(Continued)

FOREIGN PATENT DOCUMENTS

| CN | 102438688 A | 5/2012 |
| CN | 111053962 A | 4/2020 |

(Continued)

*Primary Examiner* — Rachel T Sippel
(74) *Attorney, Agent, or Firm* — McGlew and Tuttle, P.C.

(57) ABSTRACT

A connection device allows connection of an anesthetic container (400) to an anesthetic vaporizer (300) in a fluid-tight manner. A port section (1000) of the anesthetic vaporizer can be detachably connected to an adapter (1100) of the port section. With the adapter connected to the port section, a vaporizer-side channel section and a container-side channel section together form a continuous channel for anesthetic. The area of the surface of the port section that points towards the adapter is formed by a vaporizer-side contact profile (K.1, K.8), and the area of the surface of the adapter that points towards the port section is formed by a container-side contact profile (K.25, 28, 31). One contact profile has a projection (1), and the other contact profile has a corresponding recess (25) that contact with one another without an intermediate space. The projection positive-lockingly meshes with the recess.

15 Claims, 16 Drawing Sheets

(56) References Cited

U.S. PATENT DOCUMENTS

| | | | |
|---|---|---|---|
| 5,505,236 A * | 4/1996 | Grabenkort | B65D 47/38 |
| | | | 141/382 |
| 6,585,016 B1 * | 7/2003 | Falligant | A61M 16/183 |
| | | | 141/354 |
| 7,290,571 B2 | 11/2007 | Bunke et al. | |
| 2004/0206417 A1 | 10/2004 | Falligant et al. | |
| 2007/0002923 A1 | 1/2007 | Mehrtens et al. | |
| 2007/0102923 A1 * | 5/2007 | Niemela | A61M 16/183 |
| | | | 285/95 |
| 2007/0199616 A1 | 8/2007 | Chotenovsky | |
| 2010/0294277 A1 | 11/2010 | Freed | |
| 2013/0098498 A1 | 4/2013 | Cuzydlo | |

FOREIGN PATENT DOCUMENTS

| | | |
|---|---|---|
| DE | 102004043652 B3 | 10/2005 |
| EP | 0781571 A2 | 7/1997 |
| GB | 2531253 A | 4/2016 |
| WO | 2005056093 A1 | 6/2005 |
| WO | 2008151667 A1 | 12/2008 |
| WO | 2008151668 A1 | 12/2008 |
| WO | 2011070591 A2 | 6/2011 |

\* cited by examiner

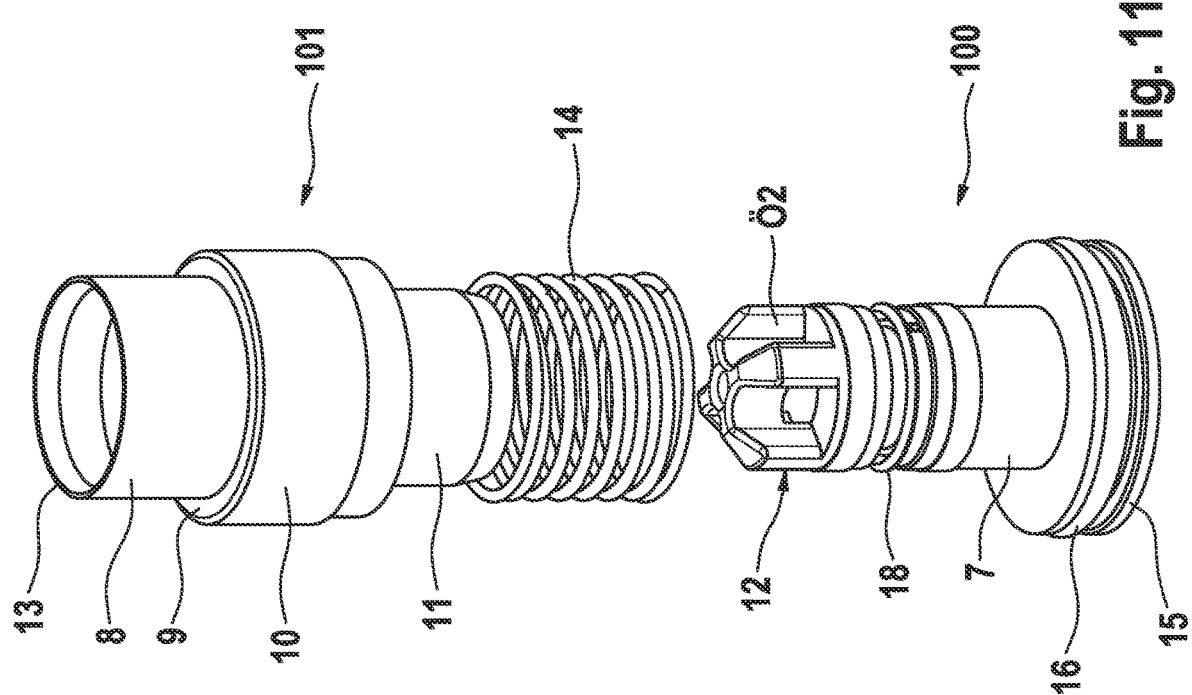
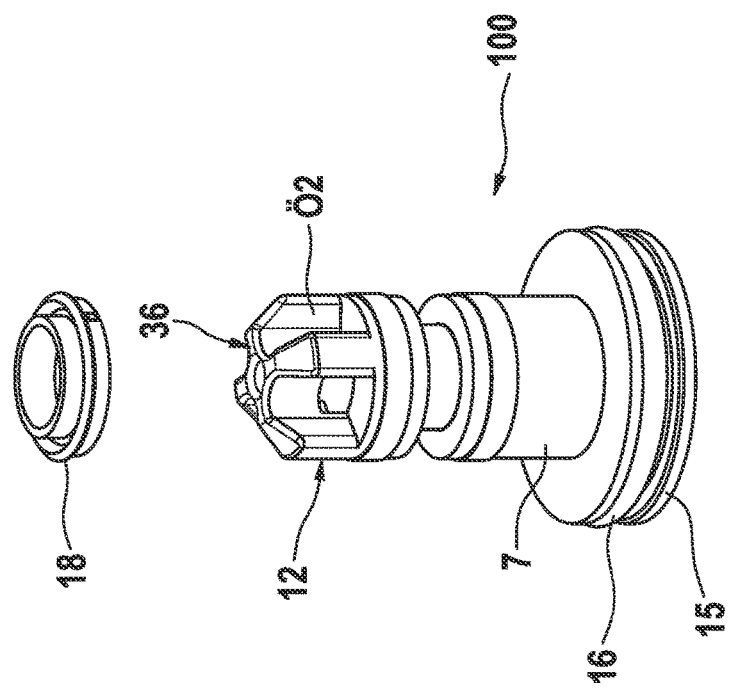

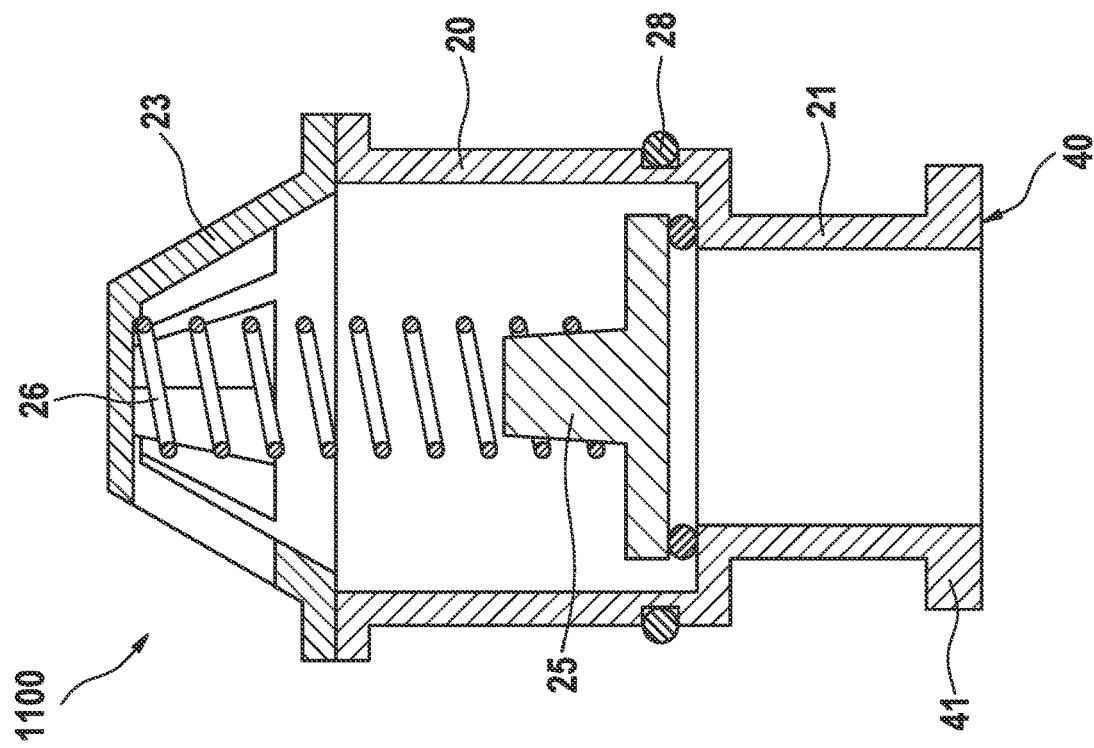
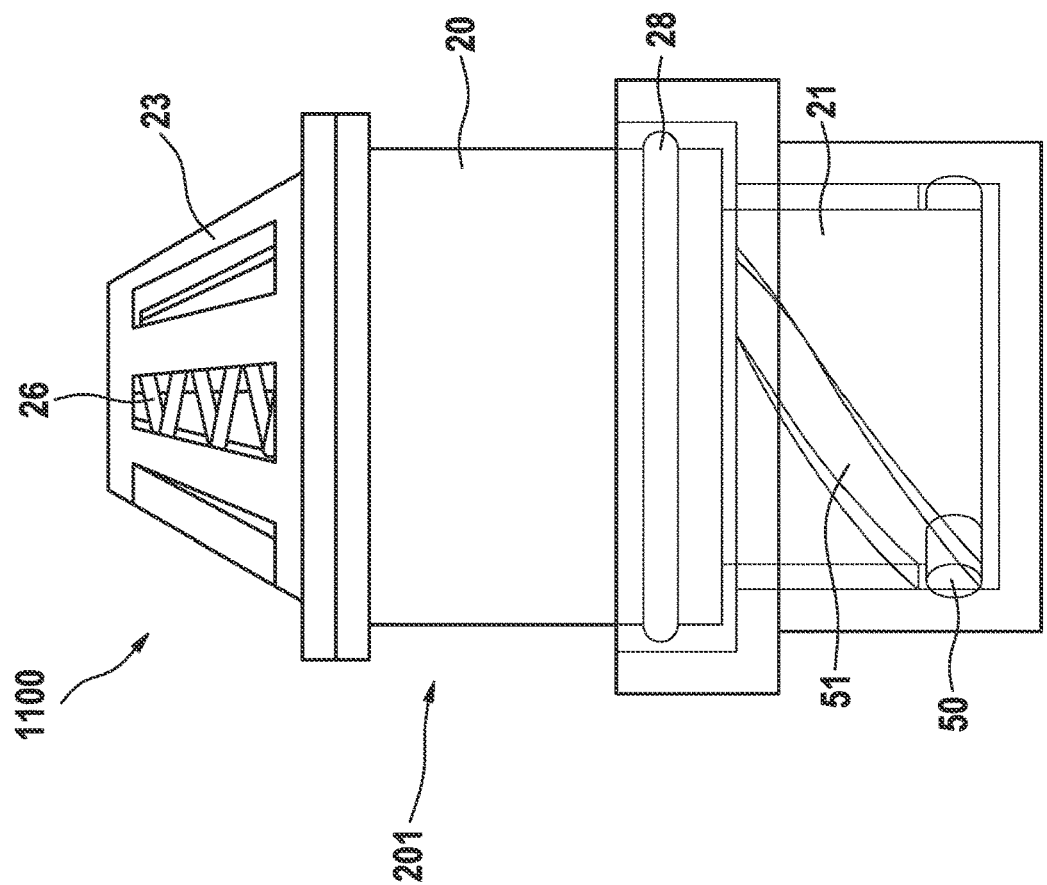
Fig. 18

CONNECTION ARRANGEMENT FOR CONNECTING AN ANAESTHETIC CONTAINER TO AN ANAESTHETIC VAPORIZER

CROSS REFERENCE TO RELATED APPLICATIONS

This application is a United States National Phase Application of International Application PCT/EP2019/069487, filed Jul. 19, 2019, and claims the benefit of priority under 35 U.S.C. § 119 of German Application 10 2018 006 264.4, filed Aug. 8, 2018, the entire contents of which are incorporated herein by reference.

TECHNICAL FIELD

The present invention pertains to a connection device, which is capable of detachably connecting an adapter of an anesthetic container to a port section of an anesthetic vaporizer and makes it possible thereby for anesthetic to flow from the anesthetic container into the anesthetic vaporizer, as well as to an anesthetic vaporizer and to an anesthetic adapter. An anesthesia device supplies a patient with a mixture of air or another gas and evaporated anesthetic. A previously liquid anesthetic is evaporated in an anesthetic vaporizer by being heated, for example, to about 40° C., and is mixed with the gas. Such an anesthetic vaporizer comprises, as a rule, an anesthetic tank. Such an anesthetic vaporizer must be filled from time to time. The liquid anesthetic is transported, as a rule, in an anesthetic container to the anesthetic device with the anesthetic vaporizer. A fluidic connection, which is, as a rule, detachable, is established there between the anesthetic container and the anesthetic vaporizer. The fluidic connection extends, as a rule, from the anesthetic container obliquely downward into the anesthetic vaporizer. After the fluidic connection has been established, the liquid anesthetic flows through this fluidic connection from the anesthetic container into the anesthetic tank of the anesthetic vaporizer.

TECHNICAL BACKGROUND

Various embodiments have become known for filling an anesthetic vaporizer with anesthetic.

DE 10 2004 043 652 B3 describes a filling device for an anesthetic vaporizer, which is configured to receive port devices of an anesthetic bottle and comprises a filling valve, which is intended to open or to close as needed, the anesthetic bottle and an anesthetic tank of the anesthetic vaporizer being connected to one another during a filling operation in the form of communicating containers via a fluid channel that can be closed by the liquid level of the anesthetic in the anesthetic tank. Further, a ventilation hole is provided, which can be opened or closed when needed, and through which an additional volume of anesthetic, which is above the liquid level in the fluid channel, can be filled into the anesthetic tank.

US 2004/0206417 A1 shows an anesthetic vaporizer (vaporizer 9) with an anesthetic tank (internal sump) and with a filling station (filling station 98). An adapter (bottle adapter 10) can be attached to a bottle containing anesthetic (anesthetic bottle 8). The adapter 10 has an adapter valve (adapter valve assembly 66) with a stem (elongated valve stem 68), which is pushed away from the anesthetic bottle 8 by a spring (bias spring 84). The filling station 98 has a stationary activation rod (stationary activation rod 160). The adapter 10 can be inserted into the filling station 98. The activation rod 160 pushes the stem 68 against the force of the spring 84 into the adapter 10, as a result of which a passage from the bottle 8 into the anesthetic tank is opened. WO 2011/070591 A1 shows an adapter 50, which can be connected to an anesthetic container (container), as well as an anesthetic vaporizer, which is connected or can be connected to a port section (receiving head, a receiver subassembly 30 attached to the vaporizer). The container can be connected to the vaporizer by a two-step movement: The adapter 40 is pushed first linearly to the port section 30 and is then rotated.

US 2007/0199616 A1 describes an adapter 10, which can be connected to a container (liquid anesthetic agent container or bottle 18) for anesthetic and has a valve assembly (movable adapter valve assembly 16). This adapter 10 can be inserted into a port (anesthetic vaporizer inlet port 68) of a vaporizer. A radial projection (radial ledge 82) in the port 68 encloses a contact pin 74. When the adapter 10 is inserted into the port 68, the radial projection 82 comes into contact with four bent connection elements 44, which open the valve device 16.

US 2013/0098498 A1 shows a device (device 10) for connecting an anesthetic container (anesthetic reservoir 70) to an anesthetic vaporizer (vaporizer). A plunger (plunger 53) closes an opening (outlet 57) in a port piece (vaporizer receiving port 52) of the vaporizer as long as the vaporizer is not connected to the container 70. The device 10 is connected to the container 70 and comprises a first component 12, which can be connected to an opening 72 of the container 10 in a fluid-tight manner, and a narrower, second component 20, which can be pushed into the port piece 52. When the device 10 is being pushed into the port piece 52, a side (downstream side) of a ram (support member 34) pointing towards the vaporizer pushes the plunger 53 into the vaporizer, so that the opening 57 is released and anesthetic can flow into the vaporizer.

SUMMARY

A basic object of the present invention is to provide a connection device for detachably connecting an anesthetic container to an anesthetic vaporizer, which makes it possible to fill an anesthetic vaporizer with anesthetic from an anesthetic container with a higher operational reliability than that of prior art connection devices. The connection device according to the present invention is configured to connect an anesthetic container to an anesthetic vaporizer from time to time in a fluid-tight manner.

The connection device comprises a port section and an adapter. The port section is connected to the anesthetic vaporizer or can be connected to it at least from time to time. The adapter is connected to the anesthetic container or can be connected to it at least from time to time.

The adapter can be detachably connected to the port section. The connection can also be severed again.

The port section comprises a vaporizer-side channel section. The adapter comprises a container-side channel section. When the adapter is connected to the port section, the vaporizer-side channel section and the container-side channel section form together a continuous channel. A fluidic connection is established by means of this continuous channel between the anesthetic container and the anesthetic vaporizer. Or such a fluidic connection can be established.

When the adapter is connected to the port section, the area of the surface of the port section that now points towards the adapter is formed by a vaporizer-side contact profile. The area of the surface of the adapter that now points towards the port section is formed by a container-side contact profile. In other words, the two surface areas provide these two contact profiles. These two contact profiles are in contact with one another without an intermediate space when the adapter is connected to the port section. "Without intermediate space" means that the volume of such an intermediate space is negligibly small, i.e., it cannot hold a relevant quantity of fluid.

The one contact profile, i.e., either the vaporizer-side contact profile or the container-side contact profile, has a projection. The other contact profile, i.e., the container-side contact profile or the vaporizer-side contact profile, has a corresponding recess. When the adapter is connected to the port section, the projection of one of the contact profiles meshes with the recess of the other contact profile in a positive-locking manner. The connection device according to the present invention makes it possible and can be used to establish a detachable fluidic connection between an anesthetic container and an anesthetic vaporizer. As a result, it is made possible to fill an anesthetic tank of the anesthetic vaporizer. The fluidic connection can again be severed, so that the anesthetic container does not hinder the insertion of the anesthetic vaporizer after severing the fluidic connection and can be filled up with additional anesthetic or be disposed of. It is possible, but not necessary, that the anesthetic vaporizer is permanently in a fluidic connection with an external reservoir for anesthetic.

The vaporizer-side channel section and the container-side channel section form a continuous channel when the adapter is connected to the port section. An anesthetic tank of the anesthetic vaporizer can be filled through this channel with anesthetic from the anesthetic container. It is possible that the fluidic connection is always formed whenever the adapter is connected to the port section and the continuous channel is established. It is also possible that a lock must also additionally be opened, especially against the force of a spring, in order to establish the fluidic connection between the anesthetic container and the anesthetic vaporizer.

When the adapter is connected to the port section, the two contact profiles are in contact with one another according to the present invention without an intermediate space. The two contact profiles do not necessarily occupy the entire space between the receiving section (port section) and the adapter. If at least one intermediate space is formed between the receiving section (port section) and the adapter because of a distance between the receiving section (port section) and the adapter, this intermediate space is in fluidic connection with the vaporizer-side channel section. The contact profiles are configured according to the present invention such that no closed intermediate space having a relevant volume is formed between the receiving section (port section) and the adapter. A large dead space is prevented by this feature according to the present invention from being able to be formed between the two contact profiles in a closed intermediate space. Liquid anesthetic may be collected in such a dead space between the two contact profiles especially during a filling operation. As soon as the adapter is separated again from the port section because the filling operation has ended, the dead space is opened and the anesthetic present in the dead space is exposed to the environment. Anesthetic typically evaporates already at room temperature, so that a relevant quantity of anesthetic evaporates abruptly after the separation in case of a large dead space, and gaseous anesthetic will escape into the environment. The frequently used anesthetic desflurane has a boiling point of about 23° C. The escape of anesthetic into the environment is undesired. The present invention prevents this undesired event.

Because the contact surfaces are in contact with one another without an intermediate space, it is also unnecessary in many cases to use a seal in order to seal such an intermediate space against anesthetic. This is especially advantageous because a contact of a liquid anesthetic with a seal may cause the seal to be attached or to swell, and a seal can thus be damaged by anesthetic. Sealants resistant to anesthetics are often expensive. In addition, a seal made of an elastic material exerts a force that is opposed to a movement of the adapter relative to the port section. This effect is sometimes undesired because this force must be overcome by applying a force. The connection device according to the present invention may, however, also comprise a seal.

According to the present invention, a projection of one contact profile meshes in a positive-locking manner with the corresponding recess of the other contact profile. It is ensured hereby that the adapter is seated in a correct position relative to the port section after the connection to the port section. It is often made possible that the adapter is guided while it is being moved towards the port section. Furthermore, the adapter is prevented from being able to be displaced laterally relative to the port section. The term "laterally" pertains to a direction of displacement in which the adapter is displaced in order to be connected to the port section.

In one embodiment, the port section comprises a hollow outer vaporizer-side component and an inner vaporizer-side component. The vaporizer-side channel section is passed through the inner vaporizer-side component. The inner vaporizer-side component and hence the vaporizer-side channel section are passed through the outer vaporizer-side component. The vaporizer-side channel section is protected therefore by two overlapping components from the environment. This configuration further reduces the risk of development of a leak and of anesthetic escaping from the vaporizer-side channel section.

The outer vaporizer-side component can preferably be moved relative to the inner vaporizer-side component, especially preferably between a blocked end position, in which the vaporizer-side channel section is blocked, and a released end position, in which this channel section is open.

In a variant of this embodiment, the outer vaporizer-side component comprises an adjusting device. The adjusting device is capable of blocking the vaporizer-side channel section in a blocked end position and of releasing the vaporizer-side channel section in a released end position. Since this adjusting device belongs to the outer rather than to the inner vaporizer-side component, the adjusting device does not compromise the flow of an anesthetic through the vaporizer-side channel section in the inner vaporizer-side component in the released end position. In the blocked end position, the adjusting device prevents the escape of anesthetic. The adjusting device preferably releases the vaporizer-side channel section as soon as the adjusting device has reached a defined intermediate position over the path from the blocked end position into the released end position. The adjusting device is preferably hollow, i.e., it encloses an interior space. The inner vaporizer-side component is passed through the adjusting device in this embodiment. The adjusting device and optionally an additional, preferably likewise hollow element of the outer vaporizer-side component are especially preferably configured as a one-part component and enclose the inner vaporizer-side component at least partially. This embodiment leads to an especially robust and mechanically simple construction. A laterally projecting part, especially a lever, is not necessary. Such a projecting part may lead to an injury or be damaged.

The port section preferably comprises a vaporizer-side spring element. This spring element is preferably supported at the inner vaporizer-side component, especially preferably at a circumferential projection of this inner component. The vaporizer-side spring element seeks to move the adjusting device into the blocked end position and to hold it in this position. The vaporizer-side spring element preferably seeks to move the adjusting device away from the anesthetic vaporizer and towards the adapter. The vaporizer-side spring element therefore contributes to the closing of the vaporizer-side channel section and to keeping it closed. In order to bring the adjusting device into the released end position or optionally at least into an intermediate position, in which a flow of anesthetic is made possible, the adjusting device must be moved against the force of the vaporizer-side spring element. This configuration leads to a further reduction of the risk of anesthetic unintentionally escaping from the port section or from the connected anesthetic vaporizer. The vaporizer-side spring element is especially preferably hollow, and it is, for example, a coil spring, and a part of the inner vaporizer-side component, by which the vaporizer-side channel section is guided, is passed through this hollow spring element. As a result, the vaporizer-side spring element does not compromise the flow of fluid through the vaporizer-side channel section.

In one embodiment, the inner vaporizer-side component is configured in the manner of a mushroom or comprises a mushroom-shaped part, i.e., the inner vaporizer-side component comprises a head and a tube. The head has a larger maximum diameter than does the tube. The vaporizer-side channel section is led through the tube or around the tube. In one embodiment, the head is seated directly on the tube; in another embodiment, a neck, which is narrower than the head, connects the head to the tube. It is possible that the vaporizer-side channel section is led through the tube and is led by the neck.

When the adjusting device is in the blocked end position, the adjusting device is preferably in contact with the head. The head consequently acts as a stop element for the adjusting device. Conversely, the application of a force to the adjusting device causes the adjusting device to move away from the head. In one embodiment, the adjusting device is in the blocked end position when it is in contact with the head, and it is in the released end position when it is moved away from the head and is located at a spaced location, especially preferably at the maximum possible distance, from the head. The vaporizer-side spring element preferably seeks to push the adjusting device against the head. The adjusting device preferably encloses the tube.

In one embodiment, at least one opening, which belongs to the vaporizer-side channel section, is recessed into the adjusting device. When the adjusting device is in the blocked end position, the head blocks the opening or each opening in the adjusting device, so that the adjusting device exerts the blocking effect and blocks the vaporizer-side channel section.

A segment of the head preferably forms an undercut. A sealing ring, which encloses the tube and closes the opening or each opening in the adjusting device and hence the vaporizer-side channel section when the adjusting device is in the blocked end position, is preferably in contact with the head.

In one embodiment, at least one opening each, which belongs to the vaporizer-side channel section, is recessed in both the inner vaporizer-side component and in the outer vaporizer-side component. At least when the adjusting device is in the released end position, and preferably also beginning from a defined intermediate position, the opening or an opening of the inner component and the opening or an opening of the outer component overlap one another and the vaporizer-side channel section is passed through these two openings and is open.

In one embodiment, the projection of the contact profile is arranged at the port section, especially preferably at the inner vaporizer-side component. The above-described head acts, for example, as the projection. The corresponding recess is arranged at the adapter, especially preferably in the container-side contact profile. The outer vaporizer-side component can be moved as a result relative to this projection.

The configuration in which the projection of the contact profile is arranged at the port section rather than at the adapter has the following advantage: The anesthetic vaporizer with the port section is used, as a rule, in an anesthetic device and is moved only together with the anesthetic device. An anesthetic container is connected, as a rule, repeatedly several times to the anesthetic vaporizer during the time during which the anesthetic vaporizer is used. The anesthetic container with the adapter is, by contrast, transported to this anesthetic device. A projection in the adapter could be pushed in unintentionally, without the adapter being connected to the port section, which causes the container-side channel section to be opened and anesthetic to flow out or otherwise to escape into the environment, which is undesirable.

In one embodiment, a housing of the outer section (port section) at least partially encloses the outer vaporizer-side component and hence also the inner vaporizer-side component. An intermediate space, preferably a gap, develops between the housing and the outer vaporizer-side component. When the adapter is connected to the port section, the adapter meshes with this intermediate space. A part of the adapter is preferably inserted into this gap.

In a variant of this embodiment, a circumferential projection of the inner vaporizer-side component is in contact from one side with the housing. The adapter is in contact with the housing from the other side. This embodiment causes a further increase in mechanical stability and to a further reduction of the risk that anesthetic will escape.

In one embodiment, the vaporizer-side channel section is passed through an element of the inner vaporizer-side component, for example, through a sleeve. An outer profile of this element, i.e., for example, of this sleeve, points towards the adjusting device. When the adjusting device is in an end position, this outer profile is flatly in contact in one embodiment with a corresponding inner profile of the adjusting device. No intermediate space, in which anesthetic can collect, preferably develops between the outer profile and the inner profile.

Since the two profiles are in contact with one another, preferably flatly, in the blocked end position, this desired effect of the adjusting device in the blocked end position can preferably be achieved without a seal. Such a seal may wear off or be attacked by the anesthetic. In one embodiment, the profiles are flatly in contact with one another when the adjusting device is in the released end position or in an intermediate position, i.e., during a filling operation. In one embodiment, the outer profile of the inner vaporizer-side component and the inner profile of the adjusting device are then flatly in contact with one another when the adjusting device is in the released end position. Or else, the shortest possible distance develops between the outer profile and the inner profile. When the adjusting device is in the blocked end position, the maximum possible distance does, by contrast, develop between the inner profile and the outer profile. This embodiment increases the mechanical stability and it further reduces the risk of escape of anesthetic when the adjusting device is in the blocked end position.

In one embodiment, an intermediate space is formed between the outer profile and the inner profile. This intermediate space is in a fluidic connection with the vaporizer-side channel section.

The adapter preferably comprises an outer container-side component and an inner container-side component. The outer container-side component is preferably hollow and it preferably accommodates in its interior the inner container-side component.

The container-side channel section is preferably passed through between the inner container-side component and the outer container-side component. This embodiment eliminates the need to prepare an opening, through which the container-side channel section is passed, in the inner container-side component.

According to the present invention, the connection device has a projection and a corresponding recess. In one embodiment, the container-side contact profile has the recess. The recess is preferably arranged in the inner container-side component.

The inner container-side component can preferably be moved relative to the outer container-side component. The adapter especially preferably comprises a container-side spring element. This container-side spring element is preferably supported at the outer container-side component. The container-side spring element seeks to move the inner container-side component towards the port section. This embodiment causes the container-side channel section to be closed or interrupted in another manner as long as the container-side spring element is in the resting position, and it is only opened when the inner container-side component is moved relative to the outer container-side component against the force of the container-side spring element. This embodiment leads to an even further reduction of the risk of the unintentional discharge of anesthetic from the anesthetic container and through the adapter.

In a variant of this embodiment, the outer container-side component comprises a support element. The container-side spring element is supported at this support element. The support element points towards the anesthetic container and is preferably arched away from the container-side contact profile. The support element especially preferably has a dome-shaped configuration. Further, the outer container-side component preferably comprises a stop element. This stop element is preferably connected mechanically to the support element. This stop element limits a movement, which the inner container-side component is capable of performing towards the anesthetic container.

This support element preferably has at least one recess. The container-side channel section is passed through the recess or at least one recess in the support element. As a result, it is not necessary to lead the container-side channel section around the support element. This embodiment increases in many cases the mechanical stability compared to other possible embodiments of the container-side channel section and/or of the support element.

According to the present invention, the port section comprises an anesthetic-side channel section. In one embodiment, this anesthetic-side channel section comprises a funnel-shaped section. This funnel-shaped section is preferably arranged at the end of the vaporizer-side channel section that faces the anesthetic vaporizer. The diameter of this funnel-shaped section increases in the direction of the anesthetic vaporizer. The funnel-shaped section correspondingly tapers in the opposite direction.

This embodiment has especially the following advantage: When an anesthetic tank of the anesthetic vaporizer is filled with anesthetic, the anesthetic flowing in displaces air or another gas from the anesthetic tank based on the higher specific gravity. This gas often contains a percentage of anesthetic. This gas shall not therefore escape into the environment, but it must enter into the anesthetic container. The anesthetic tank is frequently filled obliquely from the top. The displaced gas rises up. The funnel-shaped section collects the rising gas and guides it into the rest of the vaporizer-side channel section. The rising gas enters from there into the connected container-side channel section. The configuration with the funnel-shaped section eliminates in many cases the need to provide a separate ventilation duct to ventilate the anesthetic tank. It is, however, also possible to provide a separate ventilation duct, this ventilation duct preferably beginning in the funnel-shaped section.

According to the present invention, the two contact profiles form a projection and a recess. Both the recess and the projection are preferably rotationally symmetrical. The recess especially preferably has the shape of a truncated cone or of a cone with rounded head. The recess has the shape of a corresponding cone, which receives this truncated cone or cone. The rotationally symmetrical configuration makes it easier to connect the port section to the adapter. The rotationally symmetrical configuration eliminates the need to bring the anesthetic container first into a defined orientation relative to the anesthetic vaporizer.

The configuration of the projection as a truncated cone and that of the recess as a corresponding cone further cause the adapter and hence the anesthetic container to be held securely and not being able to tilt off. It is possible, but not necessary for a user to hold the anesthetic container during the entire filling operation. The inner vaporizer-side component and/or the inner container-side component are especially preferably likewise rotationally symmetrical.

According to the present invention, the adapter may also be connected detachably to the port section in order to establish a fluid-tight fluidic connection between the anesthetic container and the anesthetic vaporizer. A bracket preferably holds the adapter and prevents the anesthetic container with the adapter from tilting off laterally. This configuration eliminates in many cases the need for a user to have to hold the anesthetic container such that the anesthetic container will not tilt off while anesthetic is flowing into a tank of the anesthetic vaporizer.

In one embodiment of this bracket, the port section comprises a snap holder. The adapter can be inserted into the port section by a linear movement until the snap holder snaps in and holds the adapter. A user notices when the snap holder has snapped in. In another embodiment, the bracket is embodied by a bayonet connection. A weaker force, namely, only a rotary movement up to a stop, is often necessary to establish a bayonet connection than when a connection is established by a snap holder. The severing of a bayonet connection also requires a weaker force. The rotary movement of the user is converted into a torque in a predefined direction. This bayonet connection preferably comprises at least one bayonet projection and at least one corresponding bayonet recess, with which the bayonet projection or a bayonet projection meshes. It is also possible that the bayonet projection or each bayonet projection is arranged at the adapter and the bayonet recess or each bayonet recess is arranged at the port section. A combination of these two configurations is possible as well.

The port section is preferably manufactured from a metal and the adapter from a plastic. The use of a metal leads to a stable port section. Because the adapter consists of a plastic, it can yield elastically reversibly when it is connected to the port section, which leads to a further reduction of the risk of an undesired gap and hence of a dead space. In addition, compared to an adapter made of metal, metal-on-metal contact is prevented, and such a contact is often undesired. In one embodiment, the adapter can be brought, relative to the port section, into three positions and hence into three states, namely, into a spaced-apart state, into a coupled state and into a flow state. A distance develops between the two contact profiles in the spaced-apart state. The port section holds the adapter in the coupled state and prevents the adapter from being able to be moved relative to the port section at right angles or obliquely in relation to a displacement direction. The two contact profiles—or at least an area of the two contact profiles—are preferably in contact with one another without an intermediate space in the coupled state. However, at least one channel section is still blocked in the coupled state, so that no anesthetic can flow. The adapter can be brought from the coupled state into the flow state relative to the port section. The two contact profiles are in contact with one another without an intermediate space during the transfer into the flow state as well as in the flow state. The two channel sections, which are then opened, form the continuous channel in the flow state.

This embodiment makes it possible to establish the detachable fluidic connection in two steps between the adapter and the port section and hence between the anesthetic container and the anesthetic vaporizer. The adapter is brought at first into the coupled state and maintained in this state. No anesthetic can be discharged as yet in the coupled state. It is therefore possible to correct the position of the adapter. The adapter is brought into the flow state only thereafter, preferably against the force of at least one spring element. As a rule, a purely linear movement is sufficient to bring the adapter from the coupled state into the flow state. In one variant, the configuration with the coupled state is combined with the configuration in which the port section comprises an inner vaporizer-side component and an outer vaporizer-side component and the adapter comprises an inner container-side component and an outer container-side component. The outer container-side component touches the outer vaporizer-side component in the coupled state, while there is still a distance between the inner container-side component and the inner vaporizer-side component.

A preferred variant of the embodiment with the coupled state is the following: Both channel sections are still closed in the coupled state, preferably by a vaporizer-side spring element and by a container-side spring element. If the adapter is moved towards the port section and the connection device is transferred thereby from the coupled state into the flow state, the vaporizer-side channel section is opened first, preferably against the force of the vaporizer-side spring section. The container-side channel section still remains closed. The container-side channel section is also opened only during a further movement of the adapter, and a continuous channel is then made available for anesthetic. If the adapter is later again moved away from the port section and the connection device is transferred thereby from the flow state into the spaced-apart state, the container-side channel section is closed first and the vaporizer-side channel section is closed only thereafter.

This feature has the following effect, which is especially relevant when the adapter is again separated from the port section after the filling of an anesthetic tank: No anesthetic can flow from the anesthetic container into the anesthetic vaporizer as soon as the container-side channel section is closed. Anesthetic that remains in the adapter or in the port section after the closure of the container-side channel section can, however, still flow through the opened vaporizer-side channel section into the anesthetic vaporizer until the vaporizer-side channel section is closed as well. The feature thus leads to a further reduction of the risk of anesthetic escaping into the environment. The present invention further pertains to a port section for an anesthetic vaporizer, which can be detachably connected to a corresponding adapter of an anesthetic container. Furthermore, the present invention pertains to an adapter for an anesthetic container, which can be connected to a corresponding port section of an anesthetic vaporizer. The advantageous embodiments of the port section and those of the adapter of the connection device are also advantageous embodiments of this port section and of this adapter, respectively.

An anesthetic vaporizer with a port section according to the present invention comprises in one embodiment an anesthetic tank of its own. The vaporizer-side channel section is in fluidic connection with the anesthetic tank. This tank can be filled up with anesthetic from an anesthetic container, this anesthetic container comprising an adapter and the adapter and the port section forming together a connection device according to the present invention. This embodiment avoids the need for the anesthetic container to be connected to the anesthetic vaporizer during the use of the anesthetic vaporizer, i.e., during the evaporation of anesthetic. In another embodiment, the anesthetic container itself functions as an anesthetic tank, which is used during the use of the anesthetic vaporizer. This embodiment eliminates the need to have to provide a separate anesthetic tank for the anesthetic container. The anesthetic vaporizer can be made smaller.

The present invention further pertains to an anesthetic vaporizer with a port section. The port section comprises an outer vaporizer-side component (first coupling section), an inner vaporizer-side component (second coupling section) and an anesthetic guide section, the inner vaporizer-side component being arranged at least partially within the outer vaporizer-side component. The outer vaporizer-side component is capable of receiving a corresponding outer container-side counter-component (first counter-coupling section) and the inner vaporizer-side component a corresponding inner container-side counter-component (second counter-coupling section). The two counter-components belong to an adapter of an anesthetic container. The outer vaporizer-side component is formed at least partially by an adjusting device. Anesthetic can be sent from the anesthetic container into the anesthetic vaporizer by means of the anesthetic guide section. This adjusting device is mounted movably, especially displaceably relative to the inner vaporizer-side component. The movable adjusting device is capable of releasing or blocking the anesthetic guide section as desired.

Thanks to the two components (coupling sections) of the port section, the adapter can be positioned at the anesthetic vaporizer in an especially stable manner. The present invention makes it easier to avoid a relevant dead space, in which anesthetic could collect.

Furthermore, the present invention pertains to an adapter of an anesthetic container, wherein the adapter is configured for filling an anesthetic vaporizer and wherein the anesthetic vaporizer comprises a port section with an outer vaporizer-side component and with an inner vaporizer-side component. The adapter comprises an outer counter-component and an inner counter-component. The inner counter-component is arranged at least partially within the outer counter-component. The outer counter-component is mounted movably, especially displaceably relative to the inner counter-component. The movable outer counter-component is capable of releasing or blocking the anesthetic guide section as desired.

The present invention will be described below on the basis of exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 10 is a perspective view showing a first situation during the manufacture of the vaporizer-side component: Sealing ring not yet inserted;

FIG. 11 is a perspective view showing a second situation during the manufacture of the vaporizer-side component: Sealing ring inserted, inner and outer vaporizer-side components prior to the assembly;

FIG. 18 are views showing details of the bayonet connection from FIG. 17.

DESCRIPTION OF PREFERRED EMBODIMENTS

Figure 1:
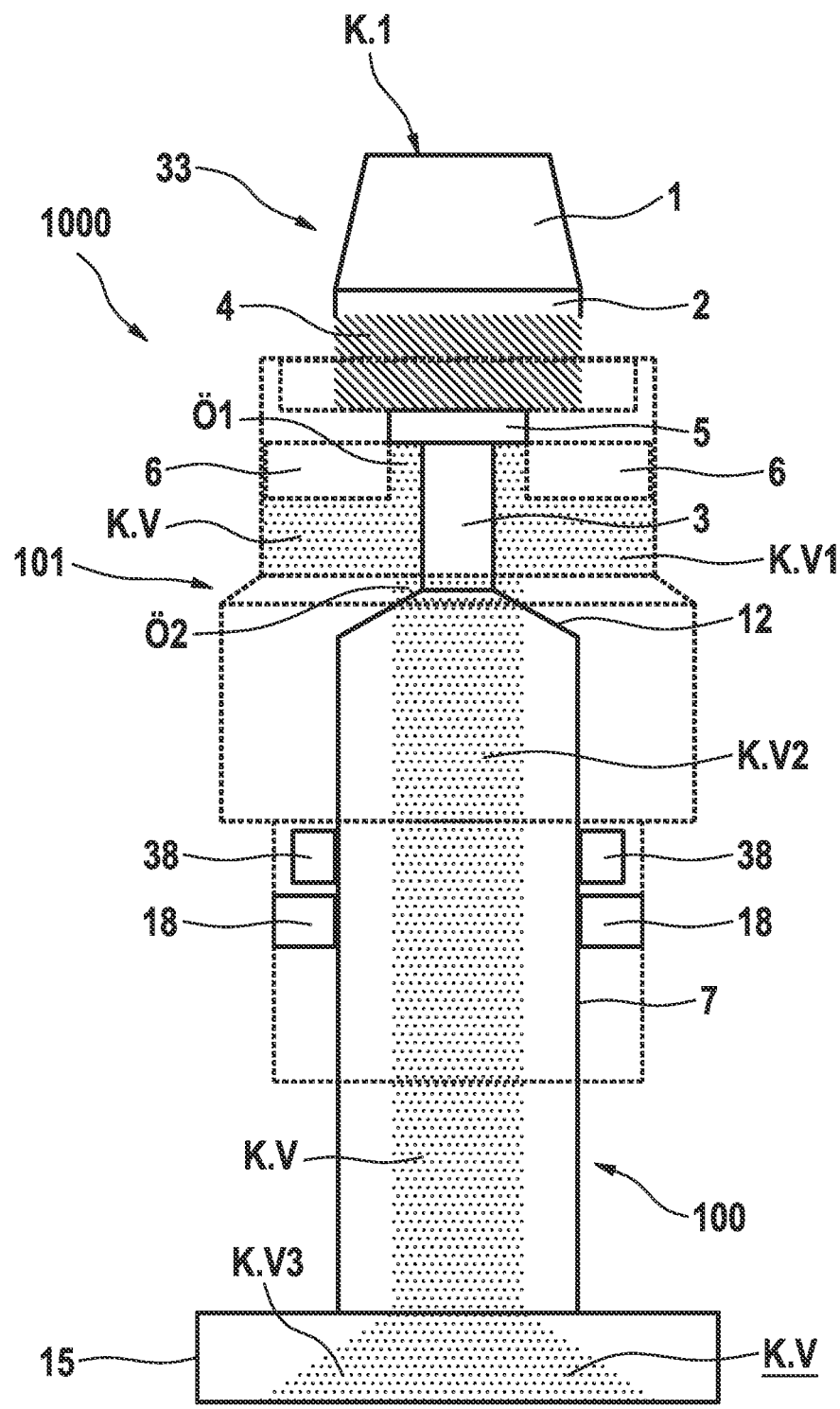
FIG. 1 is a cross-sectional view showing the inner vaporizer-side component according to a first embodiment of the port section of the anesthetic vaporizer.
Figure 2:
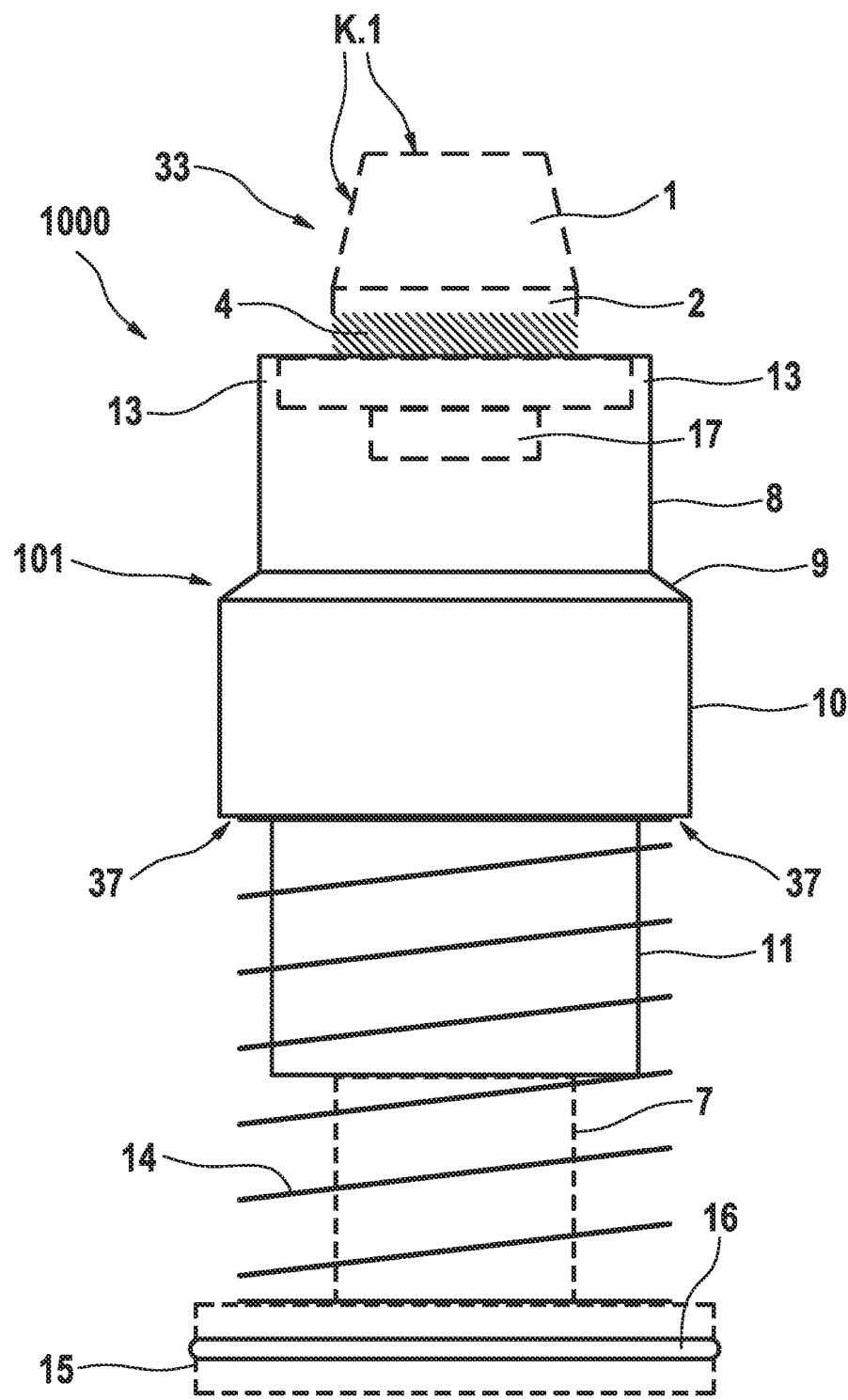
FIG. 2 is a cross-sectional view showing the outer vaporizer-side component according to the first embodiment of the port section.
Figure 3:
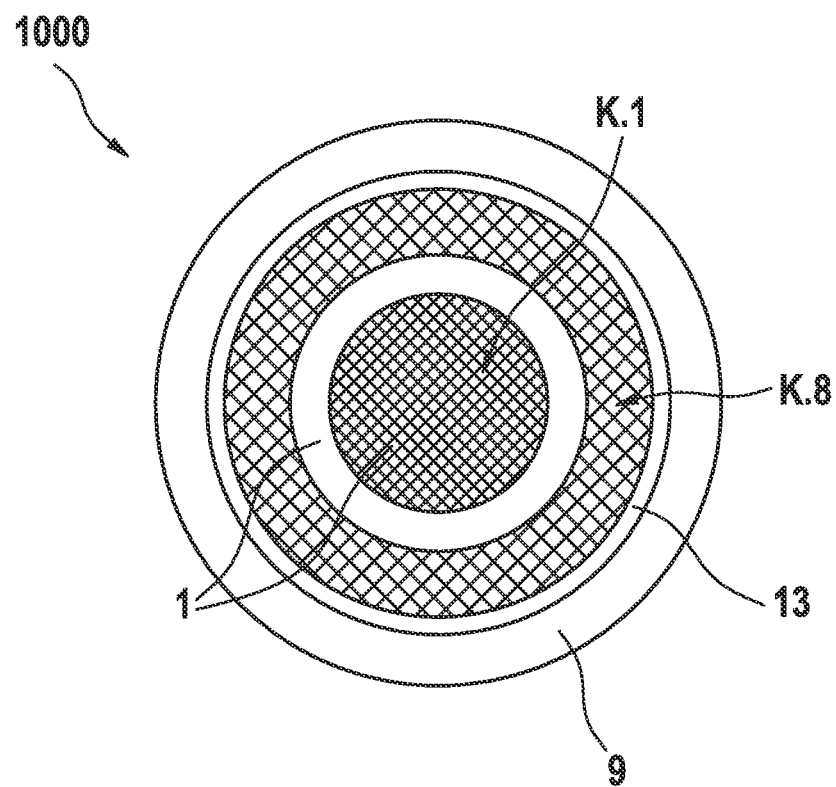
FIG. 3 is a top view showing the first embodiment of the port section in a viewing direction from the top and parallel to the central axis.
Figure 4:
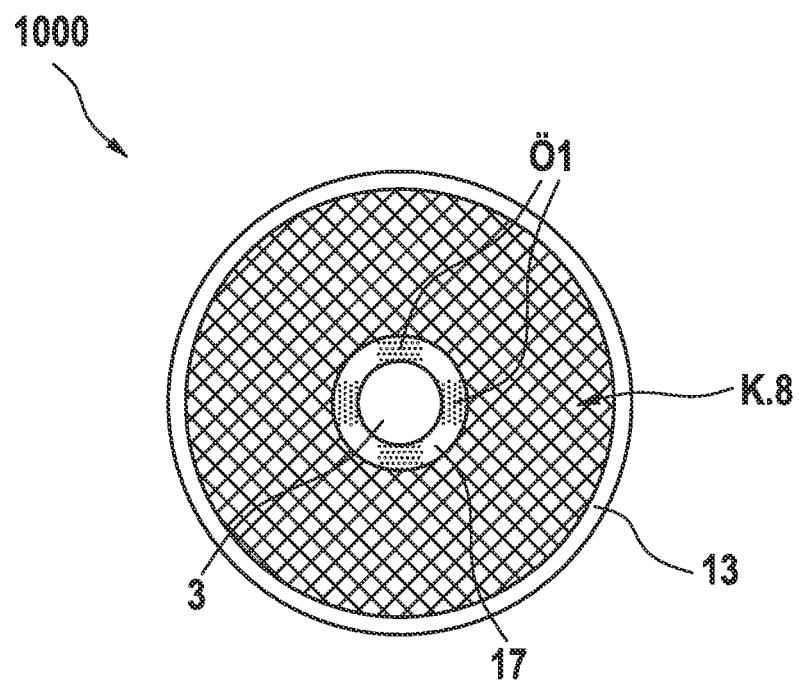
FIG. 4 is a top view showing the outer vaporizer-side component of the first embodiment of the port section in the viewing direction of FIG. 3.
Figure 5:
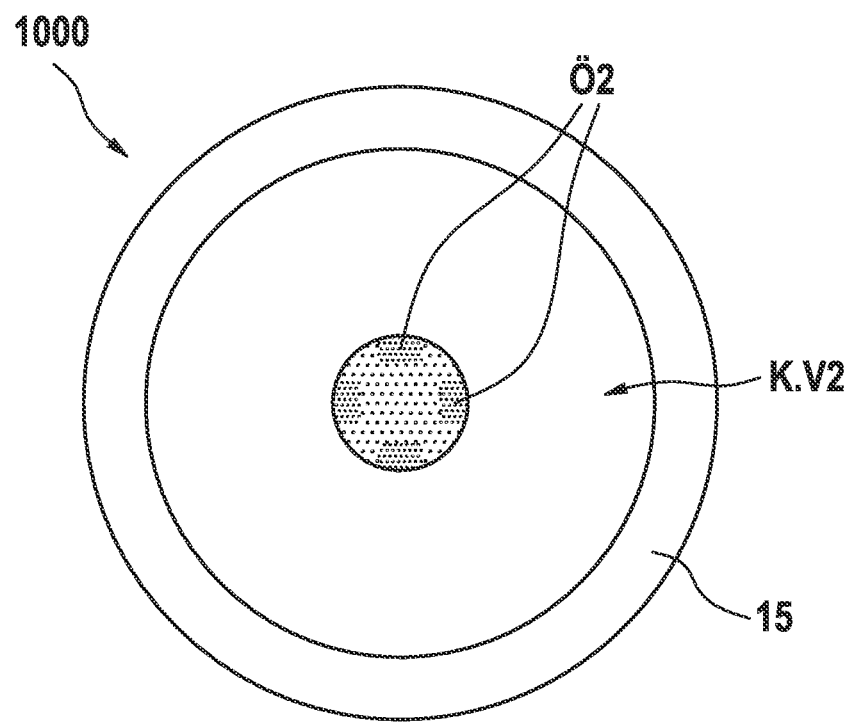
FIG. 5 is a bottom view showing the first embodiment of the port section in a viewing direction from the bottom.

Referring to the drawings, the connection device according to the exemplary embodiment comprises a port section 1000, which is inserted into an anesthetic vaporizer 300, and an adapter 1100, which is inserted into an anesthetic container 400. The port section 1000 according to the exemplary embodiment comprises an inner vaporizer-side component 100 and an outer vaporizer-side component 101. FIG. 1 through FIG. 5 show a first embodiment of the port section 1000 of the anesthetic vaporizer 300. FIG. 1 and FIG. 2 show the inner vaporizer-side component 100 and the outer vaporizer-side component 101, respectively, in a cross-sectional view through the central axis of the rotationally symmetrical port section 1000. The outer vaporizer-side component 101 is indicated by dotted lines in FIG. 1. The inner vaporizer-side component 100 is indicated by broken lines in FIG. 2. FIG. 3 and FIG. 4 show the port section 1000 in a viewing direction from the top and parallel to the central axis of the components 100 and 101, the inner vaporizer-side component 100 being omitted in FIG. 4. FIG. 5 shows the port section 1000 in a viewing direction from the bottom, which is opposite to the viewing direction of FIG. 3 and FIG. 4.

Figure 6:
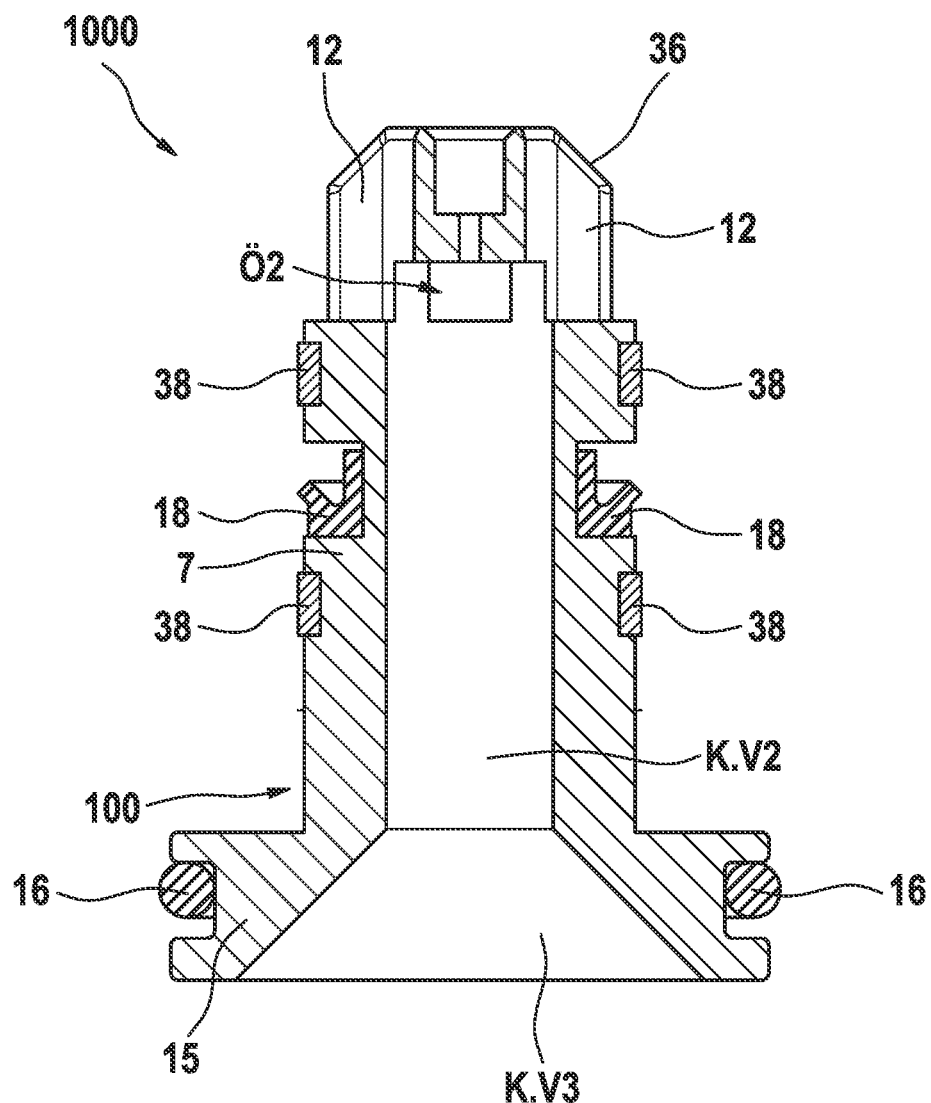
FIG. 6 is a cross-sectional view showing the inner vaporizer-side component according to a second embodiment.
Figure 7:
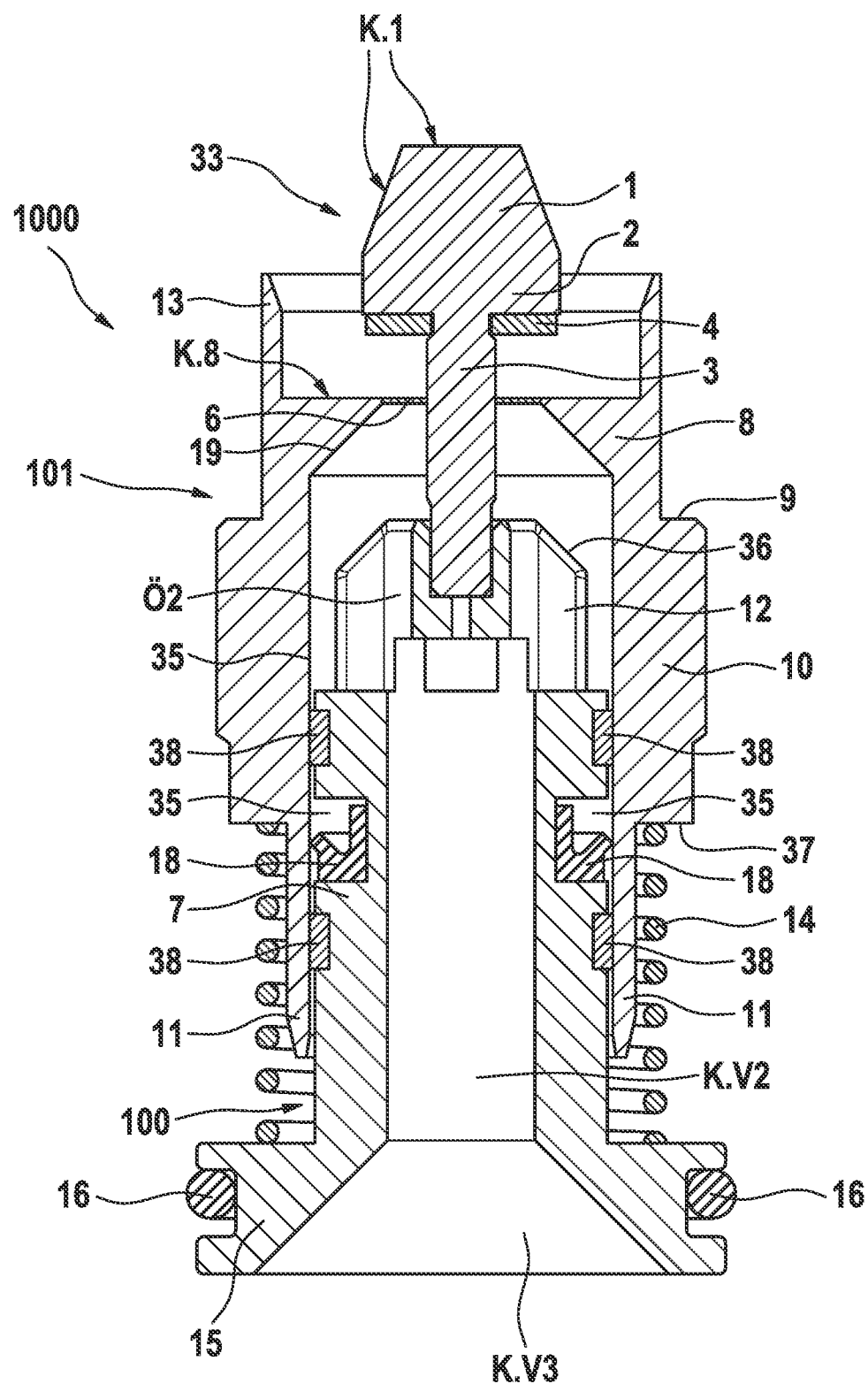
FIG. 7 is a cross-sectional view showing the entire port section according to the second embodiment.

FIG. 6 and FIG. 7 show in a cross-sectional view a second embodiment of the port section 1000. The inner vaporizer-side component 100 is shown in FIG. 6, and the entire port section 1000 of the second embodiment is shown in FIG. 7. The inner vaporizer-side component 100 comprises in both embodiments (in a sequence from top to bottom)

a head 33 with a truncated cone 1 and with an adjoining washer 2, wherein the truncated cone 1 is permanently connected to the washer 2, a circumferential sealing ring 4, which is mounted at the washer 2, a neck 3, which is preferably hollow on the inside, a washer 5 around the neck 3, which washer 5 adjoins the sealing ring 4, a collar 12, which is permanently connected to the neck 3 and receives the neck 3, an inner hollow tube 7, which is permanently connected to the collar 12, a sealing washer 18 at the outer wall of the tube 7, optionally a plurality of sliding rings 38 at the outer wall of the tube 7 (cf. FIG. 7), and a projecting washer 15 at the foot of the component 100, which is permanently connected to the tube 7.

The projecting washer 15 comprises a circumferential groove, in which a sealing ring 16 is received. All these elements preferably have a rotationally symmetrical configuration and are arranged coaxially to a central axis of the inner vaporizer-side component 100.

The mushroom-shaped head 33 has a maximum external diameter that is greater than that of the neck 3 and than that of the washer 5. In one embodiment, the entire head 33 and optionally additionally the neck 3 are manufactured from one workpiece, for example, by machining.

In the exemplary embodiment, the sealing ring 4, the sealing ring 16 and the sealing washer 18 are manufactured from an elastic material. All other elements of the inner vaporizer-side component 100 are manufactured from a solid material, preferably from a metal.

The outer vaporizer-side component 101 comprises (in a sequence from top to bottom)
- an adjusting device 8 in the form of a sleeve,
- a circumferential projection 13 at the top at the adjusting device 8, the circumferential projection 13 enclosing a flat surface in the form a circular ring,
- a collar 9, which is permanently connected to the adjusting device 8,
- a larger sleeve 10, which is permanently connected to the collar 9, i.e., the collar 9 connects the adjusting device 8 permanently to the larger sleeve 10,
- a smaller sleeve 11, which is permanently connected to the larger sleeve 10, and
- a circular ring-shaped or beveled transition surface 37 between the sleeves 10 and 11.

In one embodiment, the adjusting device 8, the larger sleeve 10 and the smaller sleeve 11 are manufactured from a single component, for example, by machining.

The port section 1000 comprises, furthermore, a vaporizer-side spring element 14 in the form of a helical compression spring, which spring element 14 encloses the smaller sleeve 11, is in contact at the bottom at the transition surface 37 with the larger sleeve 10, is supported at the projecting washer 15 and encloses the sleeve 7. The upper end of the adjusting device 8 forms a flat contact surface K.8 in the form of a circular ring, which is at right angles to the central axis of the outer vaporizer-side component 101. A circular ring-shaped recess 17 is provided in the interior of this contact surface K.8. The neck 3 is passed through this recess 17. The inner wall of the adjusting device 8 comprises a conical segment 19. The outer vaporizer-side component 101 comprises, furthermore, a cylindrical inner wall 35, which is formed by the adjusting device 8 and the two sleeves 10 and 11, cf. FIG. 7. All these elements are preferably arranged rotationally symmetrically and coaxially to a central axis of the outer vaporizer-side component 101. The central axes of both components 100 and 101 are preferably identical. Thanks to the sliding rings 38, the outer vaporizer-side component 101 can rotate relative to the inner vaporizer-side component 100 about the common central axis.

The entire outer vaporizer-side component 101 is preferably manufactured from a metal.

The outer vaporizer-side component 101 can be moved linearly along the common central axis relative to the inner vaporizer-side component 100. The vaporizer-side compression spring 14 seeks to move the outer vaporizer-side component 101 away from the washer 15 (the foot). This movement is limited in one embodiment by the circumferential sealing ring 4. In one end position, in which the compression spring 14 has reached the greatest possible length, the contact surface K.8 adjoins this sealing ring 4. The washer 5 meshes with the recess 17 in this position.

In one embodiment, the movement of the outer vaporizer-side component 101 in the opposite direction is limited by the inner profile 19 of the outer vaporizer-side component 101 touching the outer profile 36 of the inner vaporizer-side component 100. In another embodiment, the smaller sleeve 11 can reach the washer 15 when the compression spring 14 is compressed to a correspondingly great extent, and the washer 15 defines an end position.

A vaporizer-side channel section K.V, which is shown in FIG. 1 as a dotted area, is formed in the interior of the port section 1000. This vaporizer-side channel section K.V comprises

- a segment K.V1, which is arranged in the interior of the adjusting device 8,
- a segment K.V2, which is passed through the tube 7, and
- a funnel-shaped segment K.V3, which is arranged in the interior of the washer 15,
- wherein the diameter of this funnel decreases in the direction of the tube 7 and hence of the segment K.V2.

Segment K.V1 is in fluidic connection with a plurality of openings Ö1 in the contact surface K.8. These openings Ö1 adjoin the neck 3. In the end position shown in FIG. 1, the sealing ring 4 and optionally the washer 2 close these openings Ö1. This position is therefore a blocked end position of the adjusting device 8. The adjusting device 8 is then in contact with the sealing ring 4 in a positive-locking manner. The other end position is reached when the compression spring 14 is compressed to the greatest extent possible and the smaller sleeve 11 is in contact with the washer (the foot) 15 in the configuration shown in FIG. 7. This end position is the released end position of the adjusting device 8. FIG. 1 and FIG. 2 show the adjusting device 8 in the blocked end position. In the released end position, the conical inner wall 19 is flatly in contact with the outer wall 36 of the collar 12 or has—as in the configuration according to FIG. 7—the smallest possible distance to the outer wall 36. The inner wall 19 and the outer wall 36 preferably have the same profile. FIG. 7 shows an intermediate position between the released end position and the blocked end position, in which the vaporizer-side channel section K.V is already opened.

An intermediate space may develop between the inner wall 19 and the outer wall 36. This intermediate space is, however, permanently in flow connection with the anesthetic tank 304, so that no anesthetic can collect in this intermediate space.

At the end pointing towards the head 33, the tube 7 of the inner vaporizer-side component 100 is arched towards the neck 3, as a result of which the collar 12 is formed, cf. FIG. 1. A plurality of openings Ö2 are recessed into this arched end 12, cf. FIG. 5. When the adjusting device 8 is in the released end position or in an intermediate position, these openings Ö2 then connect, together with the openings Ö1, the segment K.V2 to the segment K.V1. The openings Ö2 preferably overlap—when viewed in a direction parallel to the central axis of the components 100 and 101, at least partially with the openings Ö1. The funnel-shaped segment K.V3 is permanently in fluidic connection with the segment K.V2.

The anesthetic vaporizer 300 maintains the anesthetic at a temperature of, e.g., 40° C. An anesthetic tank 304 is often under overpressure. This overpressure propagates into the segments K.V2 and K.V3 and acts in the same direction as the compression spring 14. The compression spring 14 preferably has such a strong spring force, and the openings Ö1, Ö2 are so small that the compression spring 14—supported by the overpressure—pushes the adjusting device 8 rapidly into the blocked end position, so that only a small quantity of anesthetic can escape from the anesthetic vaporizer 300.

Figure 8:
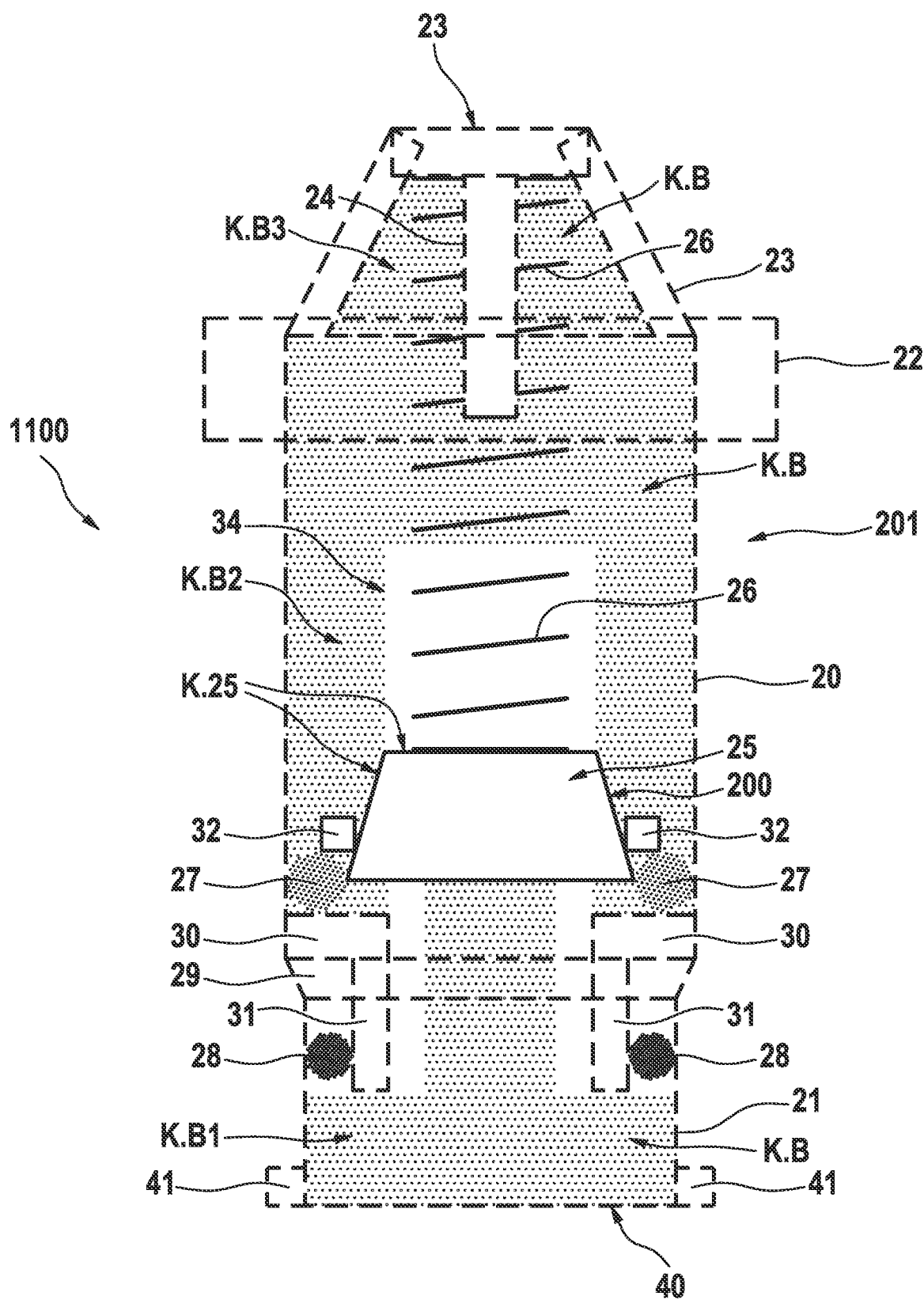
FIG. 8 is a cross-sectional view showing the adapter of the anesthetic container according to a first embodiment.
Figure 9:
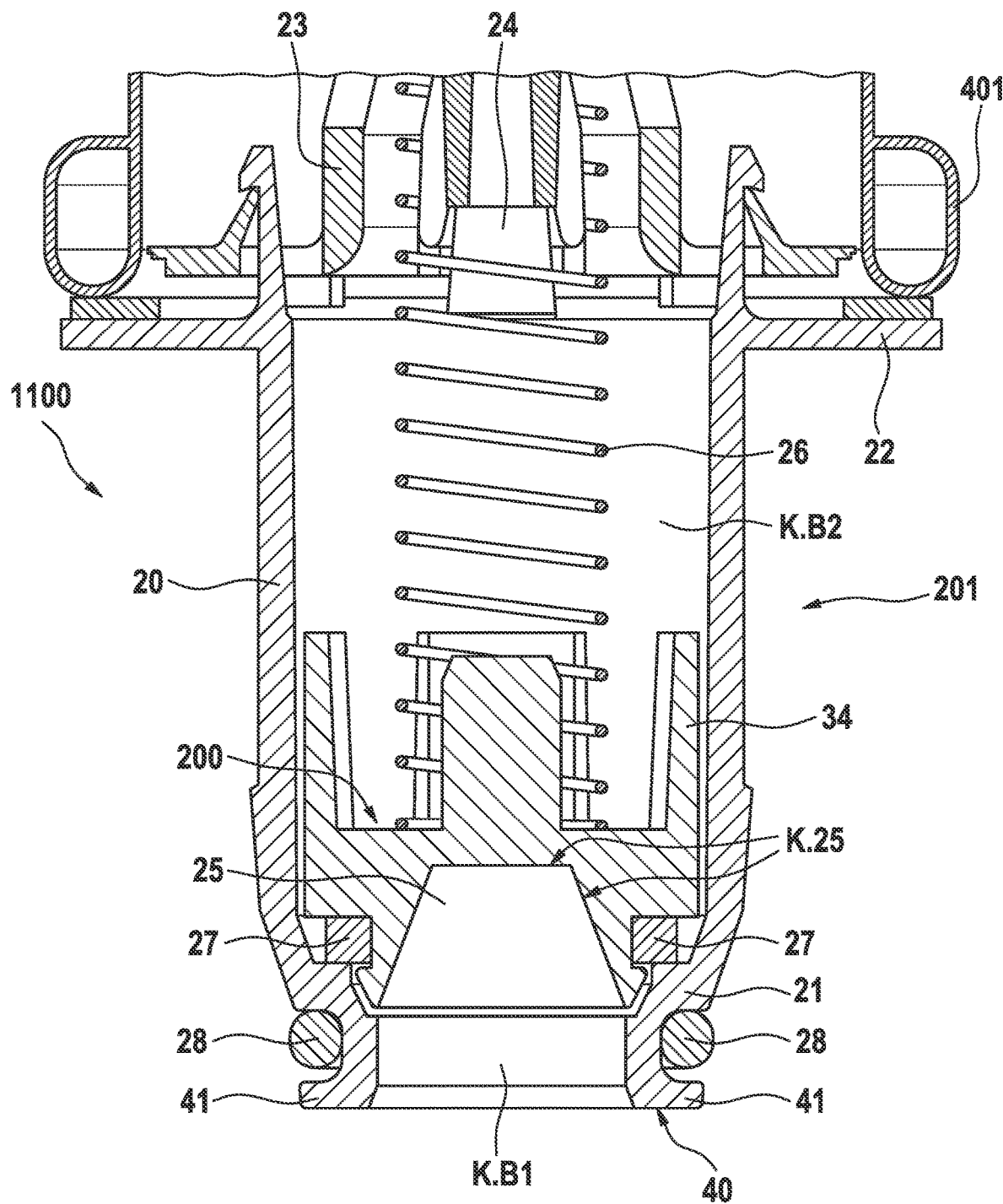
FIG. 9 is a cross-sectional view showing the adapter of the anesthetic container according to a second embodiment.
Figure 13:
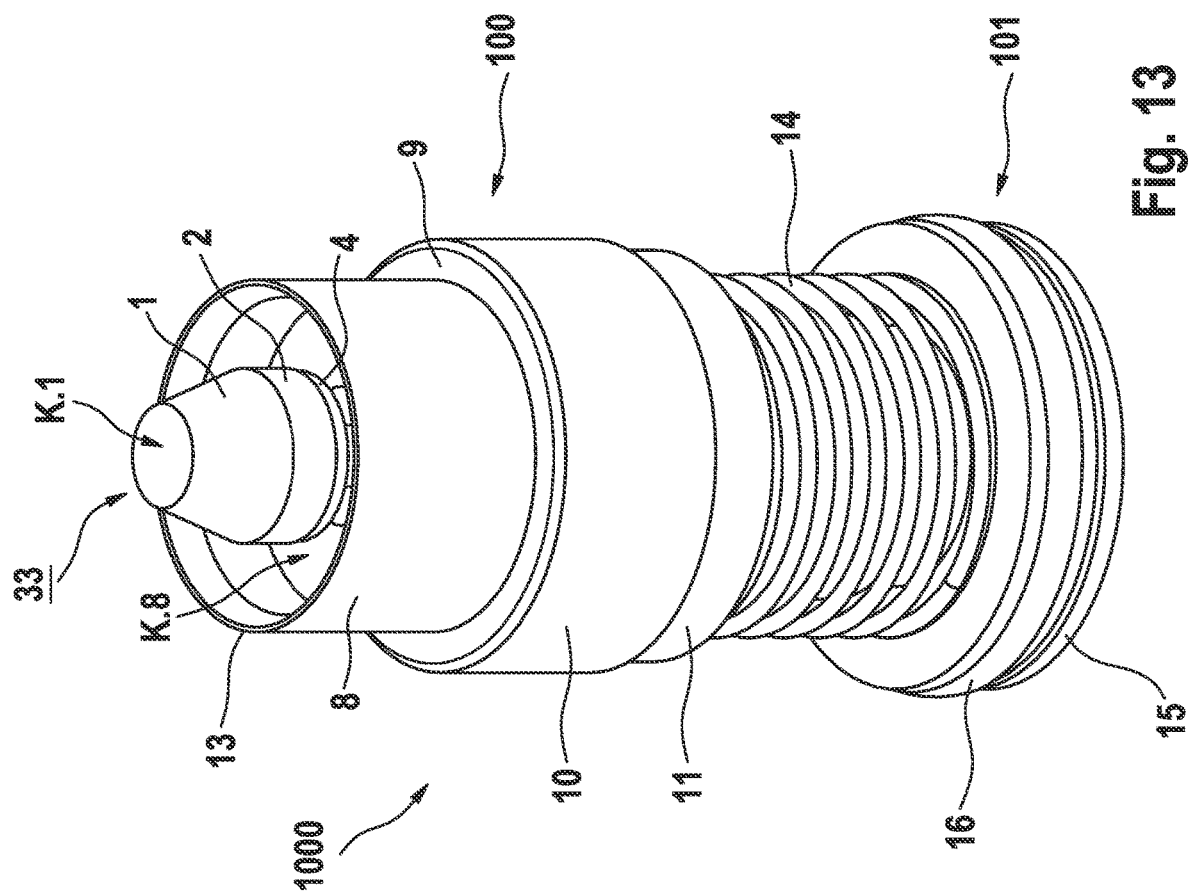
FIG. 13 is a perspective view showing a fourth situation during the manufacture of the vaporizer-side component: Component assembled.
Figure 12:
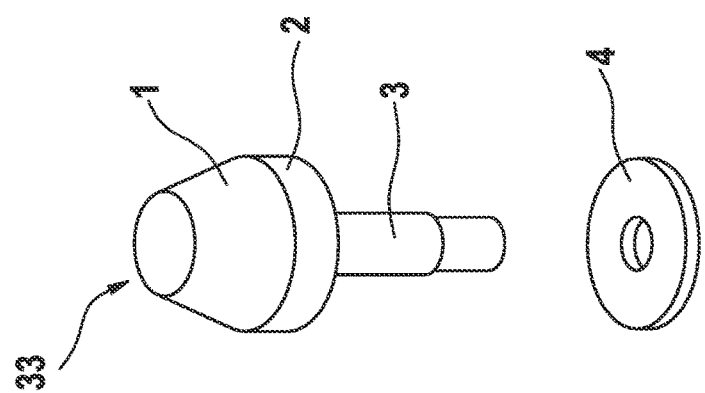
FIG. 12 is a perspective view showing a third situation during the manufacture of the vaporizer-side component: The head is placed on the sleeve of the inner vaporizer-side component.

FIG. 8 and FIG. 9 show two slightly different embodiments of the adapter 1100. This adapter 1100 is inserted into the anesthetic container 400, preferably in a detachable manner, and it comprises an inner container-side component 200 and an outer container-side component 201. The inner container-side component 200 is indicated by solid lines in FIG. 8, and the outer container-side component 201 by broken lines. The inner container-side component 200 comprises a funnel-shaped sleeve 25, a tube or sleeve 34, which is permanently connected to the funnel-shaped sleeve 25 and has openings in one embodiment (FIG. 9), a sealing ring 27, which is fastened on the outside to the sleeve 34 (FIG. 9) or to the sleeve 25 (FIG. 8), and optionally a bracket 32 for the sealing ring 27, which bracket 32 is fastened to the funnel-shaped sleeve 25.

The outer container-side component 201 comprises (from top to bottom)

a support element 23, which preferably has a dome-shaped or cylindrical configuration, i.e., arches into the anesthetic container 400, and has a plurality of recesses, a tube 24, which is fastened to the support element 23, a sealing washer 22, which is received in a corresponding opening in a wall 401 of the anesthetic container 400, a sealing ring 54, which is received in a groove of the sealing washer 22 (cf. FIG. 16), a larger sleeve 20, a circumferential washer 30, which is permanently arranged in the interior of the larger sleeve 20, a collar 29, which is permanently connected to the larger sleeve 20, a smaller sleeve 21, which is permanently connected to the collar 29, i.e., the collar 29 connects the two sleeves 20 and 21 permanently to one another, a circumferential bracket 31, which is permanently connected to the circumferential washer 30, and a sealing ring 28, which covers the space between the bracket 31 and the inner wall of the smaller sleeve 21 in one embodiment (FIG. 8) and is arranged on the outside at the larger sleeve 20 in another embodiment (FIG. 9).

Both the outer container-side component 201 and the inner container-side component 201 are preferably manufactured from a plastic, with the exception of the sealing rings 27 and 28. This embodiment reduces the weight. The adapter 1100 made of plastic can be deformed reversibly.

The adapter 1100 comprises, furthermore, a container-side spring element 26, which is supported at the support element 23, is in contact with the funnel-shaped sleeve 25 and has the shape of a compression spring.

A container-side channel section K.B, which is shown as a dotted area and comprises the following segments, is formed in the interior of the adapter 1100:

a segment K.B1, which is arranged in the interior of the smaller sleeve 21, a segment K.B2, which is arranged in the interior of the larger sleeve 20, and a segment K.B3, which is arranged in the interior of the support element 23.

The container-side compression spring 26 seeks to push the inner container-side component 200 relative to the outer container-side component 201 into an end position. In this end position, the funnel-shaped sleeve 25 separates the segment K.B1 from the segment K.B2, so that this end position is a blocked end position, in which the bracket 32 and the sealing ring 27 are in contact with the washer 30. When a force is exerted on the funnel-shaped sleeve 25 from below, i.e., through the sleeve 21, the compression spring 26 is compressed, the sleeve 25 is pushed away from the washer 30, and a fluidic connection is generated between the segment K.B1 and K.B2. The segments K.B2 and K.B3 are permanently in fluidic connection with one another.

The funnel-shaped sleeve 25 is arranged entirely in the interior of the outer container-side component 201 and has a distance to the lower end 40 of this component 201 in the direction of the central axis. As a result, the risk of the sleeve 25 being pressed unintentionally is reduced, the segments K.B1 and K.B2 are connected to one another, and the inner container-side component 200 is moved thereby from the blocked end position in the direction of the released end position and anesthetic can escape.

In the second embodiment of the adapter 1100, which is shown in FIG. 9, a circumferential contact surface 40 is flatly in contact with the contact surface K.8 of the adjusting device 8. In the first embodiment according to FIG. 8, the contact surface K.8 is, by contrast, in contact at the sealing ring 28 with the sleeve 31. In addition, a circumferential projection 41 is shown. The following is achieved in both embodiments: When the adapter 1100 is placed on the port section 1000, the container-side contact surfaces 28 and 31 or 40 come into contact with the contact surface K.8. In addition, the contact surface K.1 comes into contact with the contact surface K.25.

When the adapter 1100 is displaced farther towards the foot 15, the container-side contact surface 28 and 31 or 40 pushes the contact surface K.8, which is in contact, and hence the adjusting device 8 against the force of the compression spring 14 out of the blocked end position and into the released end position.

FIG. 10 through FIG. 13 show in a perspective view an embodiment of how the port section 1000 is assembled. The sealing washer 18 is inserted into a fitting recess in the tube 7. In addition, the sealing ring 16 is placed into the circular groove in the foot 15. FIG. 10 shows the inner vaporizer-side component 100 in a perspective view before the insertion of the sealing washer 18, and FIG. 11 shows it in a perspective view after the insertion. The adjusting device 8 with the circumferential projection 13, the collar 9, the larger sleeve 10 and the smaller sleeve 11 are permanently connected to one another. The container-side compression spring 14 and the connected parts 8, 9, 10, 11 are then pulled from the top over the tube 7, cf. FIG. 11. The sealing washer 4 is pulled from the bottom over the neck 3 and the washer 2, cf. FIG. 12. The parts are assembled, cf. FIG. 13. The two vaporizer-side components 100 and 101 cannot be separated from one another during the regular operation, but are held linearly displaceably in a coaxial position.

Figure 14:
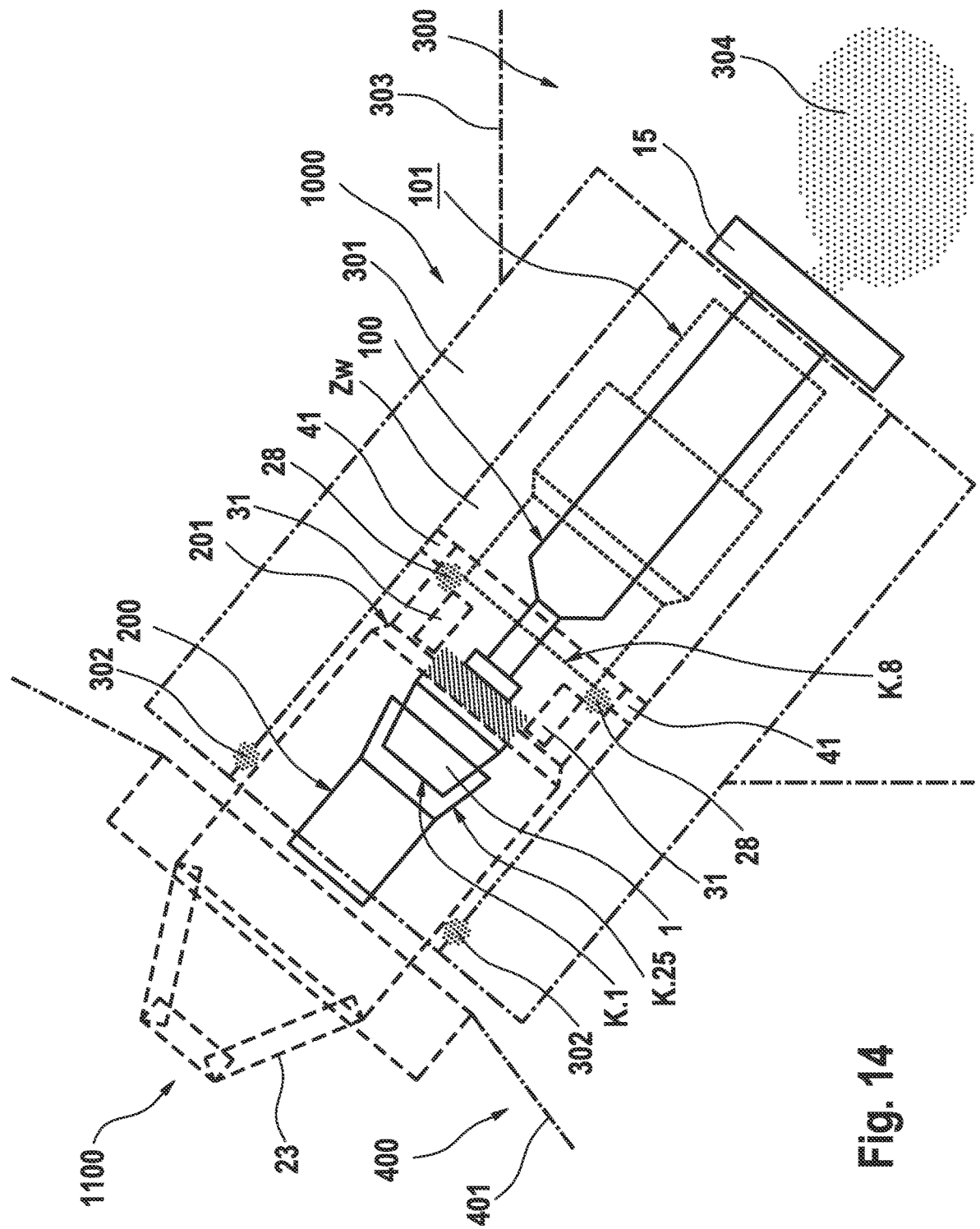
FIG. 14 is a view showing the complete connection device with the port section and with the adapter.
Figure 15:
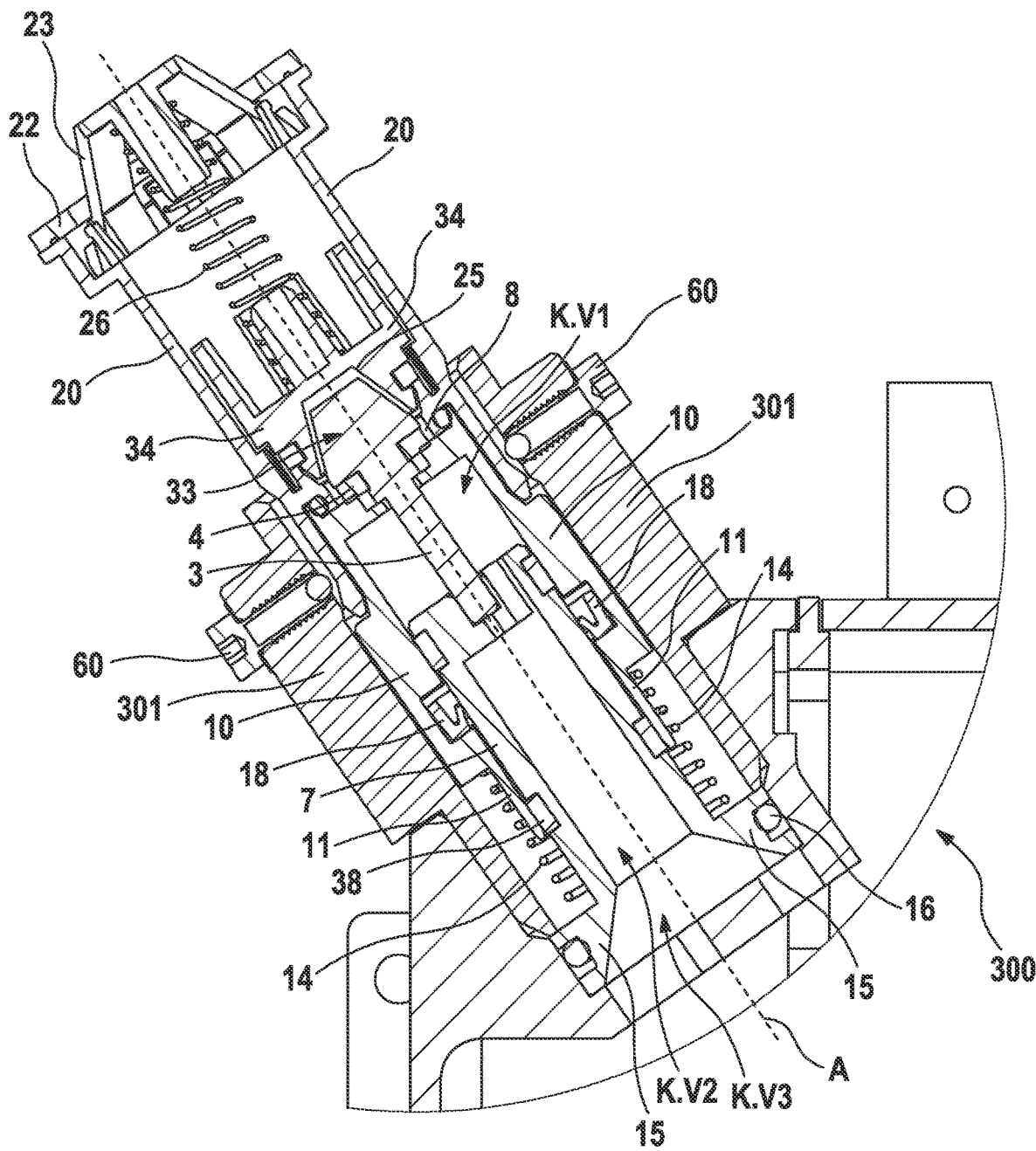
FIG. 15 is a cross-sectional view showing the complete connection device in a coupled state in a side view.
Figure 16:
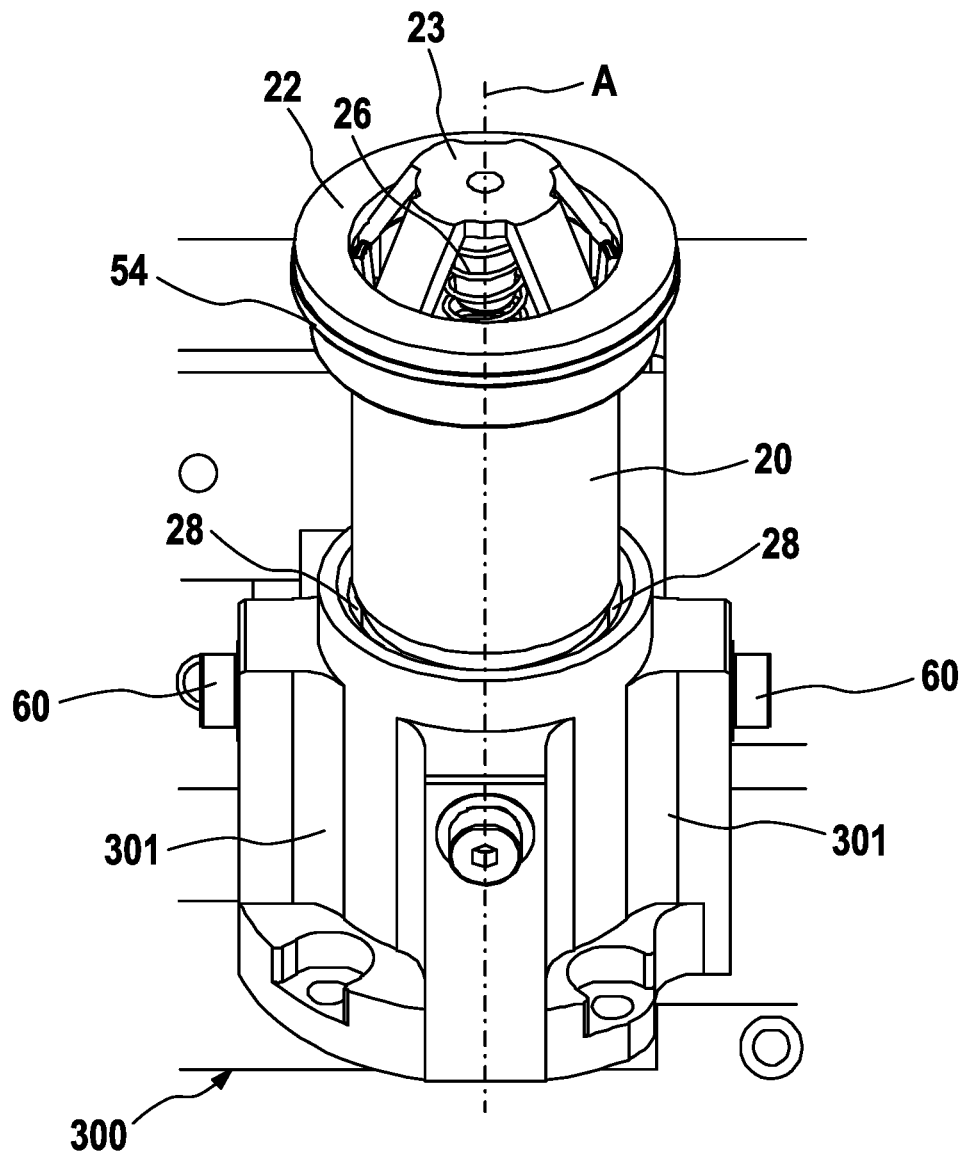
FIG. 16 is a top perspective view showing the connection device according to FIG. 15 in a top view vertically from the top.

FIG. 14, FIG. 15 and FIG. 16 show in a side view and in a top view how an anesthetic container 400 is attached with an adapter 1100 according to the present invention to an anesthetic vaporizer 300 with a port section 1000 according to the present invention. Both the adapter 1100 and the port section 1000 are preferably rotationally symmetrical about the axis A, so that it is not necessary to bring the adapter 1100 into a defined orientation relative to the port section 1000.

The anesthetic vaporizer 300 has a wall 303 which accommodates a housing 301. The housing 301, which has a cylindrical tube, which encloses the outer vaporizer-side component 101, belongs to the port section 1000. The outer vaporizer-side component 101 is held in the configuration shown in the housing 301 by means of a plurality of screws 60. These screws comprise preferably spring-mounted spherical pressure pieces, which touch the component 101. It is also possible that the component 101 is held by means of rollers at the screws 60 or without screws by means of spring elements, the spring elements optionally forming a snap holder.

On attachment, the adapter 1100 is brought first into a coupled state relative to the port section 1000. FIG. 15 shows this coupled state. The larger sleeve 20 of the adapter 1100 now meshes with the intermediate space Zw between the cylindrical inner wall of the housing 301 and the outer contour of the outer vaporizer-side component 101, it encloses the adjusting device 8 of the port section 1000 and lies on the collar 9. The circumferential projection 41 is flatly in contact with the inner wall of the housing 301. In this coupled state, the outer container-side component 201 touches the outer vaporizer-side component 101, while a distance still develops in the direction of displacement between the inner container-side component 200 and the inner vaporizer-side component 100. Contact surfaces of the adapter 1100 and of the port section 1000, which contact surfaces are located opposite each other, touch one another. The sealing ring 28 and the bracket 31 of the outer container-side component 201 are in contact according to the first embodiment according to FIG. 8 with the contact surface K.8 of the outer vaporizer-side component 101. The circumferential projection 13 compresses the sealing ring 28. In the second embodiment according to FIG. 9, the sealing ring 27 is in contact with the contact surface K.B. The contact surface K.25 of the funnel-shaped sleeve 25 and the contact surface K.1 of the truncated cone 1, on the one hand, and the sealing ring 28 in the interior of the sleeve 21 and the contact surface K.8 of the adjusting device 8, on the other hand, touch each other in FIG. 14. The contact between the contact surfaces K.25 and K.1 prevents the adapter 1100 from being moved laterally. The funnel-shaped form of the sleeve 25 and the truncated cone 1 guide together the adapter 1100 into a central position relative to the port section 1000.

The funnel-shaped sleeve 25 and the adjusting device 8 are still in a blocked state in this coupled state, and anesthetic cannot yet flow. A distance can be seen between the sleeve 15 and the head 33 with the truncated cone 1 in FIG. 15. The two still relaxed compression springs 14 and 26 maintain these blocked states in the coupled state.

The adapter 1100 is moved now linearly towards the anesthetic vaporizer 300. Depending on the configuration, the sealing ring 28 presses the contact surface K.8 of the adjusting device 8 or the sleeve 20 onto the collar 9. As a result, the adjusting device 8 and hence the entire outer vaporizer-side component 101 are displaced towards the foot 15. The adjusting device 8 is displaced into the released end position and it releases the openings Ö2. The sealing ring 4 does not cover the openings Ö1 any longer, so that the vaporizer-side channel section K.V is opened. In the example according to FIG. 15, the compression spring 14 is first compressed, namely, by the sleeve 20 pressing the sleeve 10 and by the sleeve 10 pushing together the compression spring 14. The vaporizer-side channel section K.V is opened, while the compression spring 26 is still relaxed and a distance is formed between the sleeve 25 and the head 33 and the container-side channel section K.B is therefore still blocked.

When the adapter 1100 is displaced farther towards the port section 1000 from the position shown in FIG. 15, the sleeve 25 reaches the head 33, the compression spring 26 is pushed together, and the container-side channel section K.B is opened. The container-side channel section K.B. and the vaporizer-side channel section K.V now form together a continuous channel and establish a fluidic connection from the anesthetic container 400 into the anesthetic tank 304 of the anesthetic vaporizer 300. Thanks the force of gravity, the liquid anesthetic flows through this channel obliquely downwards into the anesthetic tank 304. Only liquid anesthetic flows then in the exemplary embodiment through the channel into the anesthetic tank 304 when and as long as a user holds the anesthetic container 400 against the force of the two springs 14 and 26 in the flow state relative to the anesthetic vaporizer 300. It is ensured hereby that a user is always in the vicinity during the flow of anesthetic.

Figure 17:
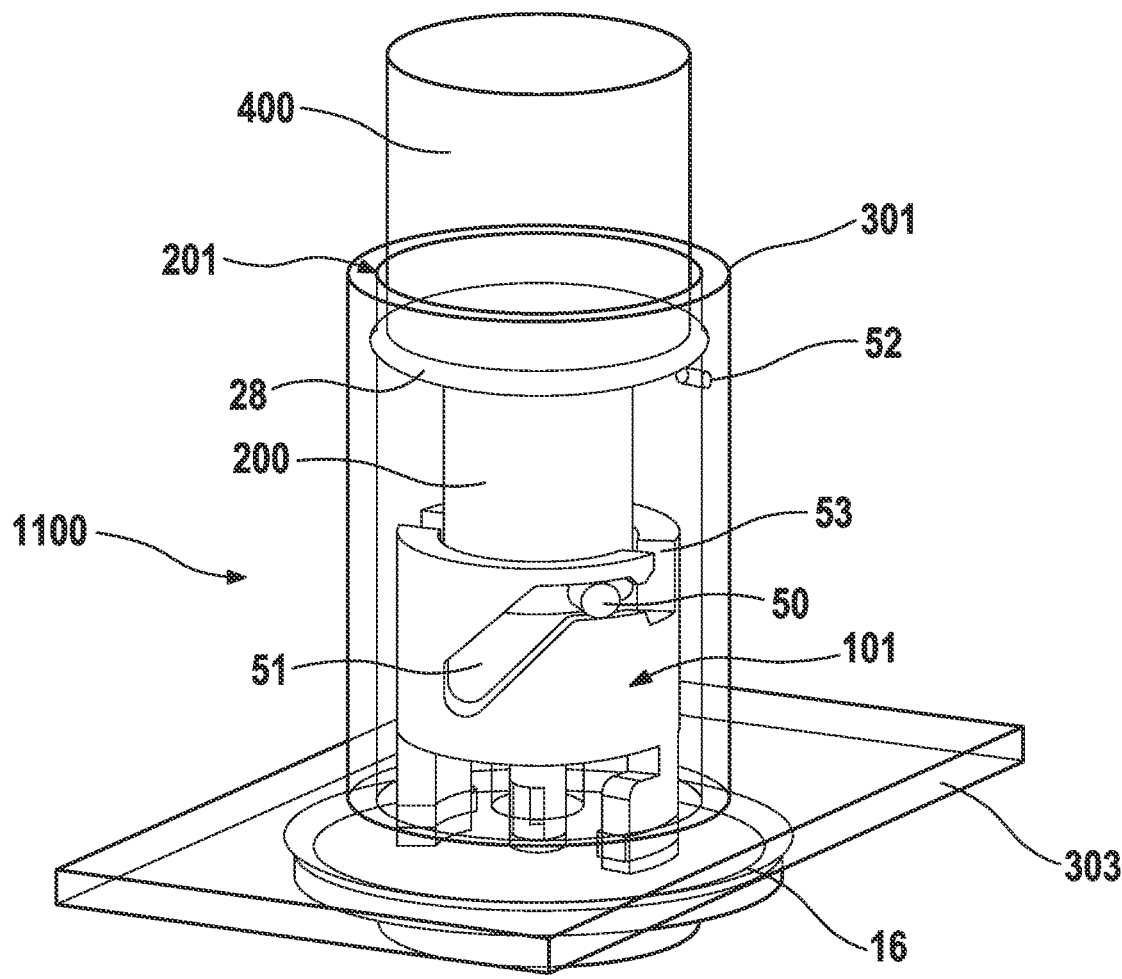
FIG. 17 is a perspective overview diagram showing a bayonet connection between a port section and an adapter.

A single channel is provided in the embodiment shown between the anesthetic container 400 and the anesthetic vaporizer 300. On the one hand, liquid anesthetic flows obliquely downward through this channel. On the other hand, gas containing evaporated anesthetic escapes from the anesthetic tank 304 through the same channel obliquely upwards. The funnel-shaped segment K.V3 in the foot 15 collects and centers rising gas and guides this gas into the segment K.V2. The risk that gas would escape from the anesthetic tank 304 into the environment is reduced thereby. FIG. 17 shows in an overview diagram a bayonet connection between the adapter 1100 and the port section 1000. FIG. 18 shows a detail view of this bayonet connection. A projection 50 at the larger sleeve 10 of the outer vaporizer-side component 101 meshes with a corresponding, obliquely arranged recess 51 at the larger sleeve 20 of the outer container-side component 201. In order to connect the adapter 1100 to the port section 1000, the projection 50 is pushed through a slot 53 in the outer vaporizer-side component 101, and the adapter 1100 is then rotated together with the projection 50 until the projection 50 reaches the end of the recess 51. The adapter 1100 is removed from the port section 1000 again by a reversed movement. In addition, an optional valve 52 is seen in FIG. 17. Gas can escape from the anesthetic tank 301 through this valve 52, while the anesthetic tank 301 is being filled with an anesthetic.

While specific embodiments of the invention have been shown and described in detail to illustrate the application of the principles of the invention, it will be understood that the invention may be embodied otherwise without departing from such principles.

The invention claimed is:

1. A connection device for the fluid-tight connection of an anesthetic container to an anesthetic vaporizer, the connection device comprising:
   a port section configured to be connected to the anesthetic vaporizer; and
   an adapter configured to be connected to the anesthetic container, wherein the adapter is detachably connectable to the port section, wherein:
   the port section comprises a vaporizer-side channel section;
   the adapter comprises a container-side channel section;
   with the adapter connected to the port section the two channel sections form a continuous channel, by means of which a fluidic connection is established or can be established between the anesthetic container and the anesthetic vaporizer;
   with the adapter connected to the port section an area of a surface of the port section that points towards the adapter is formed by a vaporizer-side contact profile;
   with the adapter connected to the port section an area of the surface of the adapter that points towards the port section is formed by a container-side contact profile;
   with the adapter connected to the port section the vaporizer-side contact profile and the container-side contact profile are in contact with one another without an intermediate space;
   one of the vaporizer-side contact profile and the container-side contact profile has a projection and the other of the vaporizer-side contact profile and the container-side contact profile has a corresponding recess;
   the projection positive lockingly meshes with the recess;
   the port section comprising:

an inner vaporizer-side component; and a hollow outer vaporizer-side component, wherein the inner vaporizer-side component is passed through the outer vaporizer-side component, and wherein the vaporizer-side channel section is passed through the inner vaporizer-side component.

2. The connection device in accordance with claim 1, wherein the outer vaporizer-side component is movable relative to the inner vaporizer-side component, wherein the outer vaporizer-side component comprises an adjusting device, wherein the adjusting device is movable relative to the inner vaporizer-side component between a blocked end position, in which the adjusting device displaces the vaporizer-side channel section, and a released end position, in which the adjusting device releases the vaporizer-side channel section.

3. The connection device in accordance with claim 2, wherein:

the adjusting device is hollow; and the inner vaporizer-side component is passed through the adjusting device.

4. The connection device in accordance with claim 2, wherein:

the inner vaporizer-side component comprises a head and a tube;

the head is fastened to the tube;

the head provides the projection of one contact profile;

the head has a larger maximum diameter than the tube;

the vaporizer-side channel section is passed through the tube; and the adjusting device is in contact with the head in the blocked end position.

5. The connection device in accordance with claim 2, wherein:

the port section comprises a housing, which encloses the outer vaporizer-side component; and with the adapter connected to the port section, the adapter meshes with an intermediate space between the housing and the outer vaporizer-side component.

6. The connection device in accordance with claim 2, wherein:

the adjusting device has an inner profile pointing towards the inner vaporizer-side component;

the inner vaporizer-side component has a segment with an outer profile pointing towards the adjusting device; and the vaporizer-side channel section is passed through said segment.

7. The connection device in accordance with claim 1, wherein the adapter comprises:

a hollow outer container-side component; and an inner container-side component, wherein:

the inner container-side component is movable relative to the outer container-side component; and the container-side channel section is passed through between the inner container-side component and the outer container-side component.

8. The connection device in accordance with claim 7, wherein the inner container-side component is movable between a blocked end position, in which the inner container-side component blocks the container-side channel section, and a released end position, in which the inner container-side component releases the container-side channel section.

9. The connection device in accordance with claim 7, wherein:

the adapter comprises a container-side spring element;

the outer container-side component comprises a support element with at least one recess;

the container-side spring element is supported at the outer container-side component and is biased to move the inner container-side component towards the port section;

the support element points towards the anesthetic container;

the container-side channel section is passed through the recess or through the at least one recess in the support element; and the container-side spring element is supported at the support element.

10. The connection device in accordance with claim 7, wherein the port section comprises:

an inner vaporizer-side component; and a hollow outer vaporizer-side component, wherein the inner vaporizer-side component is passed through the outer vaporizer-side component and wherein the vaporizer-side channel section is passed through the inner vaporizer-side component;

with the adapter connected to the port section, the outer container-side component at least partially encloses a front segment of the outer vaporizer-side component, which segment points towards the adapter; and the inner container-side component at least partially encloses a front segment of the inner vaporizer-side component, which front segment of the inner vaporizer-side component points towards the adapter.

11. The connection device in accordance with claim 1, wherein at an end facing the anesthetic vaporizer, the vaporizer-side channel section has a funnel-shaped section with a diameter that increases in a direction from the container to the anesthetic vaporizer.

12. The connection device in accordance with claim 1, wherein the adapter and port section are configured such that relative to the port section, the adapter is brought into a coupled state, in which the adapter touches the port section and the adapter meshes with the port section or the port section meshes with the adapter, but at least one channel section is still blocked, and is brought from the coupled state into a flow state, in which the two contact profiles are in contact with one another without an intermediate space and the two channel sections are open and form the continuous channel.

13. A system comprising:

an anesthetic vaporizer with a port section; and a vaporizer container with an adapter, wherein the port section and the adapter provide together a connection device for the fluid-tight connection of the anesthetic container to the anesthetic vaporizer, wherein:

the port section is connected to the anesthetic vaporizer;

the adapter is connected to the anesthetic container;

the adapter is detachably connectable to the port section;

the port section comprises a vaporizer-side channel section;

the adapter comprises a container-side channel section;

with the adapter connected to the port section the two channel sections form a continuous channel, by means of which a fluidic connection is established or can be established between the anesthetic container and the anesthetic vaporizer;

with the adapter connected to the port section an area of a surface of the port section that points towards the adapter is formed by a vaporizer-side contact profile;

with the adapter connected to the port section an area of the surface of the adapter that points towards the port section is formed by a container-side contact profile;

with the adapter connected to the port section the vaporizer-side contact profile and the container-side contact profile are in contact with one another without an intermediate space;

one of the vaporizer-side contact profile and the container-side contact profile has a projection and the other of the vaporizer-side contact profile and the container-side contact profile has a corresponding recess; and the projection positive lockingly meshes with the recess; the port section comprising:

an inner vaporizer-side component; and a hollow outer vaporizer-side component, wherein the inner vaporizer-side component is passed through the outer vaporizer-side component, and wherein the vaporizer-side channel section is passed through the inner vaporizer-side component.

14. A port section for an anesthetic vaporizer, wherein the port section is configured to be connected to an adapter of an anesthetic container in a fluid-tight manner, the port section comprising:

a vaporizer-side channel section; and a vaporizer-side contact profile with a projection, wherein:

the vaporizer-side channel section is configured to form a continuous channel together with a corresponding container-side channel section when the port section is connected to the adapter;

the vaporizer-side contact profile is configured to form an area of a surface of the port section that points towards the adapter when the adapter is connected to the port section; and the port section is configured such that with the port section connected to the adapter the vaporizer-side contact profile is in contact with a corresponding container-side contact profile without an intermediate space and the projection positive lockingly meshes with a corresponding recess of the container-side contact profile;

an inner vaporizer-side component; and a hollow outer vaporizer-side component, wherein the inner vaporizer-side component is passed through the outer vaporizer-side component, and wherein the vaporizer-side channel section is passed through the inner vaporizer-side component.

15. The port section in accordance with claim 14 in combination with an anesthetic vaporizer, wherein the port section is connected to the anesthetic vaporizer.

* * * * *